US006589767B1

(12) United States Patent
Knutzon et al.

(10) Patent No.: US 6,589,767 B1
(45) Date of Patent: Jul. 8, 2003

(54) METHODS AND COMPOSITIONS FOR SYNTHESIS OF LONG CHAIN POLYUNSATURATED FATTY ACIDS

(75) Inventors: Deborah Knutzon, Granite Bay, CA (US); Pradip Mukerji, Gahanna, OH (US); Yung-Sheng Huang, Upper Arlington, OH (US); Jennifer Thurmond, Columbus, OH (US); Sunita Chaudhary, Westerville, OH (US)

(73) Assignees: Abbott Laboratories, Abbott Park, IL (US); Calgene, LLC, Davis, CA (US)

( * ) Notice: Subject to any disclaimer, the term of this patent is extended or adjusted under 35 U.S.C. 154(b) by 0 days.

(21) Appl. No.: 09/377,452

(22) Filed: Aug. 19, 1999

Related U.S. Application Data

(62) Division of application No. 08/833,610, filed on Apr. 11, 1997, now Pat. No. 5,972,664.

(51) Int. Cl.[7] ................................................. C12N 9/02

(52) U.S. Cl. ..................................................... 435/189

(58) Field of Search ........................................ 435/189

(56) References Cited

U.S. PATENT DOCUMENTS

| | | | |
|---|---|---|---|
| 3,649,295 A | 3/1972 | Bernhart ........................ 99/57 |
| 4,058,594 A | 11/1977 | Williams ..................... 424/37 |
| 4,526,793 A | 7/1985 | Ingenbleek et al. ........... 426/72 |
| 4,526,902 A | 7/1985 | Rubin ........................ 514/560 |
| 4,614,663 A | 9/1986 | Rule ........................... 426/601 |
| 4,670,285 A | 6/1987 | Clandinin et al. .......... 426/602 |
| 4,843,095 A | 6/1989 | Rubin ........................ 514/558 |
| 4,920,098 A | 4/1990 | Cotter et al. .................... 514/2 |
| 4,938,984 A | 7/1990 | Traitler et al. .............. 426/580 |
| 5,057,419 A | 10/1991 | Martin et al. ................ 435/135 |
| 5,374,657 A | 12/1994 | Kyle ........................... 514/547 |
| 5,376,541 A | 12/1994 | Kawashima et al. ......... 435/136 |
| 5,407,957 A | 4/1995 | Kyle et al. ................... 514/547 |
| 5,443,974 A | 8/1995 | Hitz et al. ................. 435/172.3 |
| 5,492,938 A | 2/1996 | Kyle et al. .................. 514/786 |
| 5,512,482 A | 4/1996 | Voelker et al. ........... 435/320.1 |
| 5,545,553 A | 8/1996 | Gotschlich ............. 435/252.33 |
| 5,550,156 A | 8/1996 | Kyle ........................... 514/547 |
| 5,552,306 A | 9/1996 | Thomas et al. .............. 435/134 |
| 5,614,400 A | 3/1997 | Cahoon et al. ........... 435/172.3 |

FOREIGN PATENT DOCUMENTS

| | | |
|---|---|---|
| EP | 0561569 A2 | 9/1996 |
| WO | WO 93/06712 | 4/1993 |
| WO | 94/11516 | 5/1994 |
| WO | WO 94/18337 | 8/1994 |
| WO | WO 96/10086 | 4/1996 |
| WO | WO 96/21022 | 7/1996 |
| WO | WO 96/21037 | 7/1996 |

OTHER PUBLICATIONS

Voet et al. Biochemistry, 2nd Edition, John Wiley and Sons, Inc. New York, 1995.*

L.V. Michaelson, et al., "Isolation of a $\Delta^2$–Fatty Acid Desaturase Gene from *Mortierella alpina*", Journal of Biological Chemistry, American Society of Biological Chemists, vol. 273, No. 30, Jul. 24, 1998, pp. 19055–19059 (XP–002076636).

Deborah S. Knutzon, et al., "Identification of $\Delta 5$–Desaturase from *Mortierella alpina* by Heterologous Expression in Bakers' Yeast and Canola", Journal of Biological Chemistry, American Society of Biological Chemists, vol. 273, No. 45, Nov. 6, 1998, pp. 29360–29366 (XP–002106760).

Ackman, "*Problems in Fish Oils and Concentrates,*" Canadian Institute of Fisheries Technology, Technical University of Nova Scotia, 189–204, 09957.

Bajpai and Bajpai, "*Arachidonic Acid Production by Microorganism,*" Biotechnology and Applied Biochemistry 15:1–10 (1992).

Gurr, "*Alpha or Gamma*: What's a Double Bond Position Between Friends?" 1. Gamma–linolenic Acid, Lipid Technology (Mar. 1995).

Hodgson, "*Advances in Vector Systems for Gene Therapy,*" Ex. Opin. Ther. Patents 5(5): 459–468 (1995).

Horrobin, "*Medical Roles of Metabolites of Precursor EFA,*" "INFORM 6(4):428–434 (Apr. 1995).

Murata et al., "*Biosynthesis of gamma–Linolenic Acid in the Cyanobacterium Spiruline plantensis,*"In: gamma–Linolenic Acid Metabolism and Irs Roles in Nutrition and Medicine (Huang and Mills, eds.), pp. 22–32, Access Press, Chapain, IL, (1996).

(List continued on next page.)

Primary Examiner—Rebecca E. Prouty
Assistant Examiner—David Steadman
(74) Attorney, Agent, or Firm—Bingham McCutchen LLP; David W. Maher

(57) ABSTRACT

The present invention relates to a fatty acid $\Delta 5$-desaturase able to catalyze the conversion of dihomo-gamma-linolenic acid to arachidonic acid. Nucleic acid sequences encoding a $\Delta 5$-desaturase, nucleic acid sequences which hybridize thereto, DNA constructs comprising a $\Delta 5$-desaturase gene, and recombinant host microorganism or animal expressing increased levels of a $\Delta 5$-desaturase are described. Methods for desaturating a fatty acid at the $\Delta 5$ position and for producing arachidonic acid by expressing increased levels of a $\Delta 5$ desaturase are disclosed. Fatty acids, and oils containing them, which have been desaturated by a $\Delta 5$-desaturase produced by recombinant host microorganisms or animals are provided. Pharmaceutical compositions, infant formulas or dietary supplements containing fatty acids which have been desaturated by a $\Delta 5$-desaturase produced by a recombinant host microorganism or animal also are described.

22 Claims, 17 Drawing Sheets

OTHER PUBLICATIONS

Ratledge, "*Single cell oils–have they a biotechnological future?*"MB Tech. 11 (Jul. 1995).

Reddy and Thomas, "*Expression of a cyanobacterial $\Delta^6$–desaturase gene results in gamma–linolenic Acid Production in Transgenic Plants,*" Nature Biotechnology 14:639–642 (May 1996).

Ward, "*Microbial Production of long–chain PUFAs,*"INFORM 6(6):683–688 (Jun. 1995).

"*Closer to Mother's Milk*", the Gist 61:8–9 (Spring 1995).

"*Exciting Prospects for Stearidonic Acid Seed Oils,*" Lipid Technology (Nov. 1996).

Covello, P. et al., "*Functional Expression of the Extraplastidial Arabidopsis Thaliana Oleate Desturase Gene (FAD2) in Saccharomyces Cerevisiae,*" Plant Physiology, vol. 111, No. 1, pp. 223–226, (1996).

Cadena D., et al; XP–00207635: "AC C25549", EMBL Database, Jul. 24 (1997).

Hillier, L., et al; XP–002076629: *The WashU–Merck EST Project*, AC W49761, EMBL Database May 30 (1996).

Hillier, L., et al; XP–002076631: *The WashU–Merck EST Project*, AC W67716, Embl Database, Jun. 16 , (1996).

Hillier, L., et al; XP002076632: *The WashU–Merck EST Project*, AC H17219, EMBL Database, Jul. 1 (1995).

Hillier, L., et al; XP*002076633: *The WashU–Merck EST Project*, AC H19385, EMBL Database, Jul. 24 (1997).

Michaelson, L., et al; XP–002076636: *Isolation of a delta 5–Fatty Acid Desaturase Gene from Mortierella alpina*, Journal of Biological Chemistry, vol. 273, No. 30, Jul. 24 (1996).

Nathans, J.; XP–002076630: *Adult Human Retina* cDNA, EMBL database, May 14 (1996)

Spychalla, J., et al., XP–002076628: Identification of an animal w3 fatty acid desaturase by hertologous expression in Arabidopis, PNAS, vol. 94, No. 4, pp. 1142–1147, Fen. 18 (1997).

Smith et al. "The ERG3 Gene In Saccharomyces–Cerevisiae Is Required For The Utilization Of Respiratory Substrates And In Heme–Deficient Cells" Yeast, 1993, vol. 9, No. 11, pp. 1177–1187.

\* cited by examiner

```
GCTTCCTCCA GTTCATCCTC CATTTCGCCA CCTGCATTCT TTACGACCGT TAAGCAAG
                                                              60*

ATG GGA ACG GAC CAA GGA AAA ACC TTC ACC TGG GAA GAG CTG GCC
met Gly Thr Asp Gln Gly Lys Thr Phe Thr Trp Glu Glu Leu Ala CAT AAC ACC AAG GAC CTA CTC TTG GCC ATC CGC AGG GTG TAC
His Asn Thr Lys Asp Leu Leu Leu Ala Ile Arg Arg Val Tyr
            120*

GAT GTC ACA AAG TTC TTG AGC CGC CAT CCT GGT GGA GTG ACT CTC
Asp Val Thr Lys Phe Leu Ser Arg His Pro Gly Gly Val Thr Leu
                                    180*

CTG CTC GGA GCT GGC CGA GAT GTT ACT ATT ATC CCG GTC TTT GAG
Leu Leu Gly Ala Gly Arg Asp Val Thr Ile Ile Pro Val Phe Glu

GCG TTT GGG GCT GCA GAT ATT ATC ATG AAG TAC TAT GTG ATG TAT
Ala Phe Gly Ala Ala Asp Ile Ile Met Lys Tyr Tyr Val Met Tyr
                                                240*

CTG GTC TCG AAT GAG CTG CCC ATC TTC CCG GAG CCA ACG GAT CGG
Leu Val Ser Asn Glu Leu Pro Ile Phe Pro Glu Pro Thr Asp Arg
 300*

AAA ACC ATC AAG AGA GTC GAG GGC TAC TTT ACG GTG TTC
Lys Thr Ile Lys Arg Val Glu Gly Tyr Phe Thr Val Phe
        360*

GTC CAC ACA TAC CAC ATT
Val His Thr Tyr His Ile                        AAC ATT
                                                Asn Ile
```

```
GAT CCC AAG AAT AGA CCA GAG ATC CGA GGA TAC GCT CTT ATC TTT
Asp Pro Lys Asn Arg Pro Glu Ile Arg Gly Tyr Ala Leu Ile Phe
                                          420*           480*

GGA TCC TTG ATC GCT TCC TAC TAC CTC CAG CGA GGA CCT TTC GTT
Gly Ser Leu Ile Ala Ser Tyr Tyr Leu Gln Arg Gly Pro Phe Val

GTC GAA CGC ACA TGG CTT CAG GTG TTT GCA ATC CTC ATG GGA TTT
Val Glu Arg Thr Trp Leu Gln Val Phe Ala Ile Leu Met Gly Phe
540*

GCG TGC GCA CAA GTC GGA CTC AAC GAT CAT GCA ATC ATC TCT CAC
Ala Cys Ala Gln Val Gly Leu Asn Asp His Ala Ile Ile Ser His
                    600*

TCA GTG ACC CAC AAC CCC ACT GTC CCT CTT CAT ATT GAT TCT CAC
Ser Val Thr His Asn Pro Thr Val Pro Leu His Ile Asp Ser His
                                                660*

GAC TTT TTC AAC GGA GCA TCG TAC TGG AAG ATT CTG GGA TAC CAA GCC ACG
Asp Phe Phe Asn Gly Ala Ser Tyr Trp Lys Ile Leu Gly Tyr Gln Ala Thr

CTC GGC CAT CAC CCC TAC ACC AAC ATT GCT GGA GCA GAT CCC GAC CAT ATG CAC
Leu Gly His His Pro Tyr Thr Asn Ile Ala Gly Ala Asp Pro Asp His Met His
                                                    720*
```

```
TCG ACG TCT GAG CCC GAT GTT CTC ATC AAG CCC AAC CAA TGG
Ser Thr Ser Glu Pro Asp Val Leu Ile Lys Pro Asn Gln Trp
780*

TTT GTC AAC CAC ATC ATT AAC CAG GTT CGT CTC ATC AAG TAC GGA
Phe Val Asn His Ile Ile Asn Gln Val Arg Leu Ile Lys Tyr Gly
        840*

CTG CTG GCG TTC AAG GTG CGC ATG TTT CTG CAG CAC CTG TAC TTT
Leu Leu Ala Phe Lys Val Arg Met Phe Leu Gln His Leu Tyr Phe

GTC AAG ACC AAT GAC GCT ATT ATC GAC AAT ATC AAC ATT TAC CAC
Val Lys Thr Asn Asp Ala Ile Ile Asp Asn Ile Asn Ile Tyr His
                                900*

ACT GTG ATG TTC TGG GGC GGC TAT CTG CCC AAT CCC ATC TCG ACA TGG CTG
Thr Val Met Phe Trp Gly Gly Tyr Leu Pro Asn Pro Ile Ser Thr Trp Leu
                                                960*

ATT GTT CCC CTG CAG TAT CTG TCG TCT TAC TGG TTT GTG AAG GTG CTG CTC TTG
Ile Val Pro Leu Gln Tyr Leu Ser Ser Tyr Trp Phe Val Lys Val Leu Leu Leu

ACG GTC GCG GAC ATG GTG TCG ACG GCG CTG CTG GCG CTG ACC TTC CAG
Thr Val Ala Asp Met Val Ser Thr Ala Leu Leu Ala Leu Thr Phe Gln
1020*
```

FIG. 3C

```
GCG AAC CAC GTT GAG GAA GTT CAG TGG CCG TTG CCT GAC GAG AAC
Ala Asn His Val Glu Glu Val Gln Trp Pro Leu Pro Asp Glu Asn
     1080                      1140
GGG ATC CAA AAG GAC GAT TGG GCA GCT ATG CAG GTC GAG ACT ACG CAG
Gly Ile Gln Lys Asp Asp Trp Ala Met Gln Val Glu Thr Thr Gln
                                    1200
GAT TAC GCA CAC GAT TCG CAC CTC TGG ACC AGC ATC ACT GGC AGC TTG
Asp Tyr Ala His Asp Ser His Leu Trp Thr Ser Ile Thr Gly Ser Leu
AAC TAC CAG GCT GTG CAC CAT CTG CTT CCC AAC GTG TCG CAG CAC CAT
Asn Tyr Gln Ala Val His His Leu Phe Pro Asn Val Ser Gln His His
1260
TAT CCC GAT ATT CTG GCC ATC ATC AAG AAC ACC TGC AGC GAG TAC AAG
Tyr Pro Asp Ile Leu Ala Ile Ile Lys Asn Thr Cys Ser Glu Tyr Lys
              1320
GTT CCA TAC CTT GTC AAG GAT ACG TTT TGG CAA GCA TTT GCT TCA CAT
Val Pro Tyr Leu Val Lys Asp Thr Phe Trp Gln Ala Phe Ala Ser His
                                        1380
TTG GAG CAC TTG CGT GTT CTT GGA CTC CGT CCC AAG GAA GAG TAGA
Leu Glu his Leu Arg Val Leu Gly Leu Arg Pro Lys Glu Glu
                                              1440
AGAAAAAAAG CGCCGAATGA AGTATTGCCC CCTTTTCTC CAAGAATGGC AAAAGGAGAT

CAAGTGGACA TTCTCTATGA AGA
```

FIG. 3D

```
        10         20         30         40         50         60
                                                                  *
LHHTYTNIAG ADPDVSTSEP DVRRIKPNQK WFVNHINQHM FVPFLYGLLA FKVRIQDINI 70         80         90        100        110        120
                                                                  *
LYFVKTNDAI RVNPISTWHT VMFWGGKAFF VWYRLIVPLQ YLPLGKVLLL FTVADMVSSY 130        140        150        160        170        180
                                                                  *
WLALTFQANY VVEEVQWPLP DENGIIQKDW AAMQVETTQD YAHDSHLWTS ITGSLNYQXV

HHLFPH
```

```
MA29     LFPNVSQHHYPDILAIIKNTCSEYKVPYLVKDTFWQAFASHLEHLRVLGLRPKE----------E  446
MA524    LFPSMPRHNFSKIQPAVETLCKKYNVRYHT-TGMIEGTAEVFSRLNEVSKAASKMGKAQ        457
BorD6    LFPKMPRCNLRKISPYVIELCKKHNLPYNY-ASFSKANEMTLRTLRNTALQARDITKPLPKNLVWEALHT  446
Sy6803D6 LFPNICHIHYPQLENIIKDVCQEFGVIEYKVYPTFKAAIIASNYRWLEAMGKAS             359
Sp1D6    LFPHICHIHYPKIAPILAEVCEEFGVNYAVHQTFFGALAANYSWLKKMSINPET------        365
```

FIG. 5C

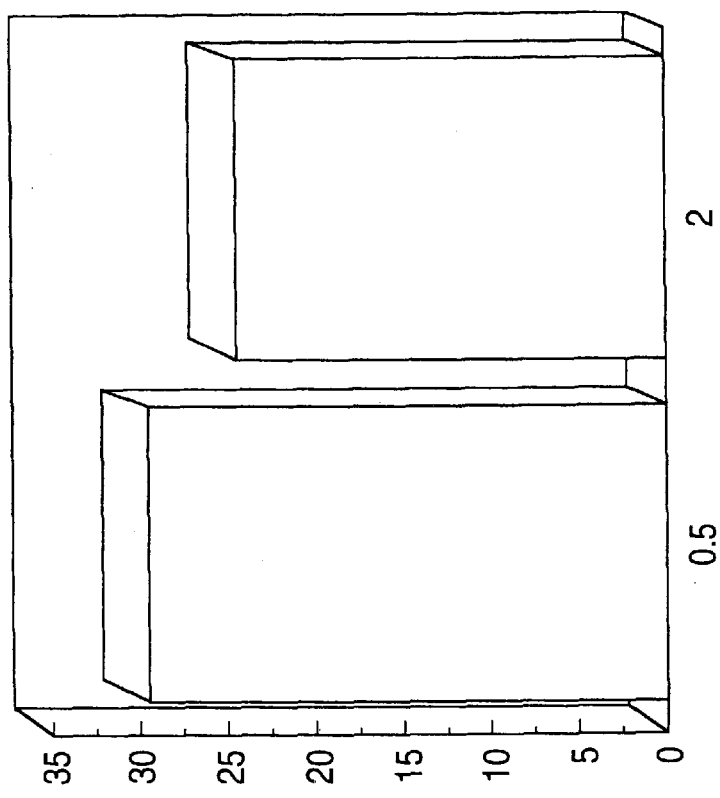

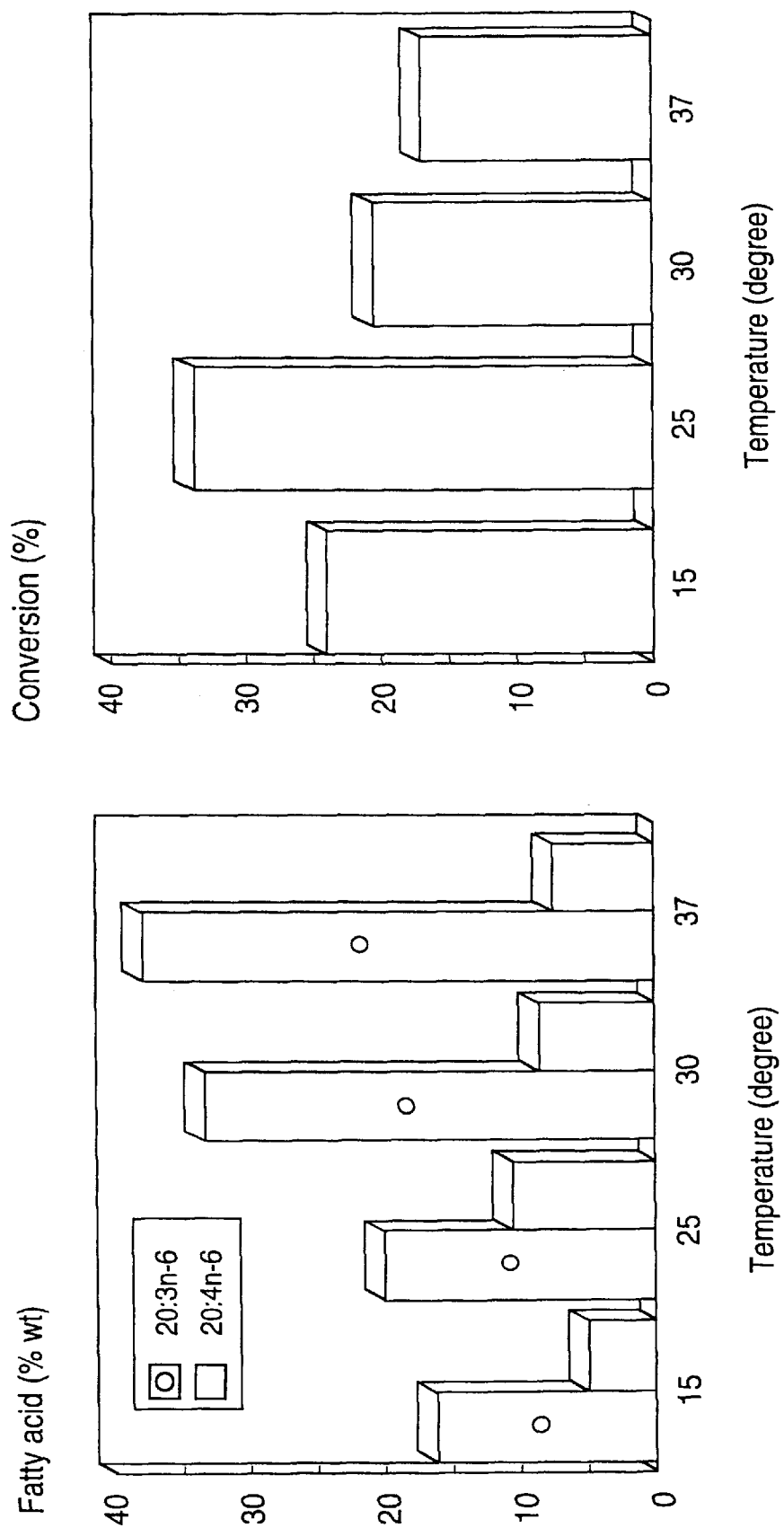

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 1483 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

GCTTCCTCCA GTTCATCCTC CATTTCGCCA CCTGCATTCT TTACGACCGT TAAGCAAGAT      60

-continued

```
GGGAACGGAC CAAGGAAAAA CCTTCACCTG GGAAGAGCTG GCGGCCCATA ACACCAAGGA      120

CGACCTACTC TTGGCCATCC GCGGCAGGGT GTACGATGTC ACAAAGTTCT TGAGCCGCCA      180

TCCTGGTGGA GTGGACACTC TCCTGCTCGG AGCTGGCCGA GATGTTACTC CGGTCTTTGA      240

GATGTATCAC GCGTTTGGGG CTGCAGATGC CATTATGAAG AAGTACTATG TCGGTACACT      300

GGTCTCGAAT GAGCTGCCCA TCTTCCCGGA GCCAACGGTG TTCCACAAAA CCATCAAGAC      360

GAGAGTCGAG GGCTACTTTA CGGATCGGAA CATTGATCCC AAGAATAGAC CAGAGATCTG      420

GGGACGATAC GCTCTTATCT TTGGATCCTT GATCGCTTCC TACTACGCGC AGCTCTTTGT      480

GCCTTTCGTT GTCGAACGCA CATGGCTTCA GGTGGTGTTT GCAATCATCA TGGGATTTGC      540

GTGCGCACAA GTCGGACTCA ACCCTCTTCA TGATGCGTCT CACTTTTCAG TGACCCACAA      600

CCCCACTGTC TGGAAGATTC TGGGAGCCAC GCACGACTTT TTCAACGGAG CATCGTACCT      660

GGTGTGGATG TACCAACATA TGCTCGGCCA TCACCCCTAC ACCAACATTG CTGGAGCAGA      720

TCCCGACGTG TCGACGTCTG AGCCCGATGT TCGTCGTATC AAGCCCAACC AAAAGTGGTT      780

TGTCAACCAC ATCAACCAGC ACATGTTTGT TCCTTTCCTG TACGGACTGC TGGCGTTCAA      840

GGTGCGCATT CAGGACATCA ACATTTTGTA CTTTGTCAAG ACCAATGACG CTATTCGTGT      900

CAATCCCATC TCGACATGGC ACACTGTGAT GTTCTGGGGC GGCAAGGCTT TCTTTGTCTG      960

GTATCGCCTG ATTGTTCCCC TGCAGTATCT GCCCCTGGGC AAGGTGCTGC TCTTGTTCAC     1020

GGTCGCGGAC ATGGTGTCGT CTTACTGGCT GGCGCTGACC TTCCAGGCGA ACCACGTTGT     1080

TGAGGAAGTT CAGTGGCCGT TGCCTGACGA GAACGGGATC ATCCAAAAGG ACTGGGCAGC     1140

TATGCAGGTC GAGACTACGC AGGATTACGC ACACGATTCG CACCTCTGGA CCAGCATCAC     1200

TGGCAGCTTG AACTACCAGG CTGTGCACCA TCTGTTCCCC AACGTGTCGC AGCACCATTA     1260

TCCCGATATT CTGGCCATCA TCAAGAACAC CTGCAGCGAG TACAAGGTTC ATACCTTGT      1320

CAAGGATACG TTTTGGCAAG CATTTGCTTC ACATTTGGAG CACTTGCGTG TTCTTGGACT     1380

CCGTCCCAAG GAAGAGTAGA AGAAAAAAAG CGCCGAATGA AGTATTGCCC CCTTTTTCTC     1440

CAAGAATGGC AAAAGGAGAT CAAGTGGACA TTCTCTATGA AGA                      1483
```

(2) INFORMATION FOR SEQ ID NO:2:

(i) SEQUENCE CHARACTERISTICS:
        (A) LENGTH: 446 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:2:

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95
```

```
Lys Thr Ile Lys Thr Arg Val Glu Gly Tyr Phe Thr Asp Arg Asn Ile
            100                 105                 110
Asp Pro Lys Asn Arg Pro Glu Ile Trp Gly Arg Tyr Ala Leu Ile Phe
        115                 120                 125
Gly Ser Leu Ile Ala Ser Tyr Tyr Ala Gln Leu Phe Val Pro Phe Val
    130                 135                 140
Val Glu Arg Thr Trp Leu Gln Val Val Phe Ala Ile Ile Met Gly Phe
145                 150                 155                 160
Ala Cys Ala Gln Val Gly Leu Asn Pro Leu His Asp Ala Ser His Phe
                165                 170                 175
Ser Val Thr His Asn Pro Thr Val Trp Lys Ile Leu Gly Ala Thr His
            180                 185                 190
Asp Phe Phe Asn Gly Ala Ser Tyr Leu Val Trp Met Tyr Gln His Met
        195                 200                 205
Leu Gly His His Pro Tyr Thr Asn Ile Ala Gly Ala Asp Pro Asp Val
    210                 215                 220
Ser Thr Ser Glu Pro Asp Val Arg Arg Ile Lys Pro Asn Gln Lys Trp
225                 230                 235                 240
Phe Val Asn His Ile Asn Gln His Met Phe Val Pro Phe Leu Tyr Gly
                245                 250                 255
Leu Leu Ala Phe Lys Val Arg Ile Gln Asp Ile Asn Ile Leu Tyr Phe
            260                 265                 270
Val Lys Thr Asn Asp Ala Ile Arg Val Asn Pro Ile Ser Thr Trp His
        275                 280                 285
Thr Val Met Phe Trp Gly Gly Lys Ala Phe Phe Val Trp Tyr Arg Leu
    290                 295                 300
Ile Val Pro Leu Gln Tyr Leu Pro Leu Gly Lys Val Leu Leu Leu Phe
305                 310                 315                 320
Thr Val Ala Asp Met Val Ser Ser Tyr Trp Leu Ala Leu Thr Phe Gln
                325                 330                 335
Ala Asn His Val Val Glu Glu Val Gln Trp Pro Leu Pro Asp Glu Asn
            340                 345                 350
Gly Ile Ile Gln Lys Asp Trp Ala Ala Met Gln Val Glu Thr Thr Gln
        355                 360                 365
Asp Tyr Ala His Asp Ser His Leu Trp Thr Ser Ile Thr Gly Ser Leu
    370                 375                 380
Asn Tyr Gln Ala Val His His Leu Phe Pro Asn Val Ser Gln His His
385                 390                 395                 400
Tyr Pro Asp Ile Leu Ala Ile Ile Lys Asn Thr Cys Ser Glu Tyr Lys
                405                 410                 415
Val Pro Tyr Leu Val Lys Asp Thr Phe Trp Gln Ala Phe Ala Ser His
            420                 425                 430
Leu Glu His Leu Arg Val Leu Gly Leu Arg Pro Lys Glu Glu
        435                 440                 445
```

(2) INFORMATION FOR SEQ ID NO:3:

(i) SEQUENCE CHARACTERISTICS:
        (A) LENGTH: 186 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

-continued

```
Leu His His Thr Tyr Thr Asn Ile Ala Gly Ala Asp Pro Asp Val Ser
1               5                   10                  15

Thr Ser Glu Pro Asp Val Arg Arg Ile Lys Pro Asn Gln Lys Trp Phe
            20                  25                  30

Val Asn His Ile Asn Gln His Met Phe Val Pro Phe Leu Tyr Gly Leu
                35                  40                  45

Leu Ala Phe Lys Val Arg Ile Gln Asp Ile Asn Ile Leu Tyr Phe Val
    50                  55                  60

Lys Thr Asn Asp Ala Ile Arg Val Asn Pro Ile Ser Thr Trp His Thr
65                  70                  75                  80

Val Met Phe Trp Gly Gly Lys Ala Phe Phe Val Trp Tyr Arg Leu Ile
                85                  90                  95

Val Pro Leu Gln Tyr Leu Pro Leu Gly Lys Val Leu Leu Leu Phe Thr
                100                 105                 110

Val Ala Asp Met Val Ser Ser Tyr Trp Leu Ala Leu Thr Phe Gln Ala
                115                 120                 125

Asn Tyr Val Val Glu Val Gln Trp Pro Leu Pro Asp Glu Asn Gly
    130                 135                 140

Ile Ile Gln Lys Asp Trp Ala Ala Met Gln Val Glu Thr Thr Gln Asp
145                 150                 155                 160

Tyr Ala His Asp Ser His Leu Trp Thr Ser Ile Thr Gly Ser Leu Asn
                165                 170                 175

Tyr Gln Xaa Val His His Leu Phe Pro His
                180                 185
```

(2) INFORMATION FOR SEQ ID NO:4:

(i) SEQUENCE CHARACTERISTICS:
        (A) LENGTH: 457 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
                35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
                100                 105                 110

Ser Leu Gly Tyr Tyr Asp Ser Ser Lys Ala Tyr Tyr Ala Phe Lys Val
                115                 120                 125

Ser Phe Asn Leu Cys Ile Trp Gly Leu Ser Thr Val Ile Val Ala Lys
                130                 135                 140

Trp Gly Gln Thr Ser Thr Leu Ala Asn Val Leu Ser Ala Ala Leu Leu
145                 150                 155                 160
```

-continued

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Val Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455

(2) INFORMATION FOR SEQ ID NO:5:

(i) SEQUENCE CHARACTERISTICS:
        (A) LENGTH: 446 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

```
Lys Ser Leu Ala Gly Gln Glu Val Thr Asp Ala Phe Val Ala Phe His
     50                  55                  60

Pro Ala Ser Thr Trp Lys Asn Leu Asp Lys Phe Phe Thr Gly Tyr Tyr
 65              70                  75                      80

Leu Lys Asp Tyr Ser Val Ser Glu Val Ser Lys Val Tyr Arg Lys Leu
                 85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
            115                 120                 125

Tyr Gly Val Leu Phe Cys Glu Gly Val Leu Val His Leu Phe Ser Gly
            130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
            195                 200                 205

Asp Pro Asp Leu Gln Tyr Ile Pro Phe Leu Val Val Ser Ser Lys Phe
            210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala Gln Glu Leu Leu Gly
            275                 280                 285

Cys Leu Val Phe Ser Ile Trp Tyr Pro Leu Leu Val Ser Cys Leu Pro
290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
            355                 360                 365

Gly Leu Gln Phe Gln Ile Glu His His Leu Phe Pro Lys Met Pro Arg
            370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
            420                 425                 430

Lys Pro Leu Pro Lys Asn Leu Val Trp Glu Ala Leu His Thr
            435                 440                 445
```

(2) INFORMATION FOR SEQ ID NO:6:

(i) SEQUENCE CHARACTERISTICS:

(A) LENGTH: 359 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:6:

```
Met Leu Thr Ala Glu Arg Ile Lys Phe Thr Gln Lys Arg Gly Phe Arg
1               5                   10                  15

Arg Val Leu Asn Gln Arg Val Asp Ala Tyr Phe Ala Glu His Gly Leu
            20                  25                  30

Thr Gln Arg Asp Asn Pro Ser Met Tyr Leu Lys Thr Leu Ile Ile Val
        35                  40                  45

Leu Trp Leu Phe Ser Ala Trp Ala Phe Val Leu Phe Ala Pro Val Ile
50                  55                  60

Phe Pro Val Arg Leu Leu Gly Cys Met Val Leu Ala Ile Ala Leu Ala
65                  70                  75                  80

Ala Phe Ser Phe Asn Val Gly His Asp Ala Asn His Asn Ala Tyr Ser
                85                  90                  95

Ser Asn Pro His Ile Asn Arg Val Leu Gly Met Thr Tyr Asp Phe Val
            100                 105                 110

Gly Leu Ser Ser Phe Leu Trp Arg Tyr Arg His Asn Tyr Leu His His
        115                 120                 125

Thr Tyr Thr Asn Ile Leu Gly His Asp Val Glu Ile His Gly Asp Gly
130                 135                 140

Ala Val Arg Met Ser Pro Glu Gln Glu His Val Gly Ile Tyr Arg Phe
145                 150                 155                 160

Gln Gln Phe Tyr Ile Trp Gly Leu Tyr Leu Phe Ile Pro Phe Tyr Trp
                165                 170                 175

Phe Leu Tyr Asp Val Tyr Leu Val Leu Asn Lys Gly Lys Tyr His Asp
            180                 185                 190

His Lys Ile Pro Pro Phe Gln Pro Leu Glu Leu Ala Ser Leu Leu Gly
        195                 200                 205

Ile Lys Leu Leu Trp Leu Gly Tyr Val Phe Gly Leu Pro Leu Ala Leu
210                 215                 220

Gly Phe Ser Ile Pro Glu Val Leu Ile Gly Ala Ser Val Thr Tyr Met
225                 230                 235                 240

Thr Tyr Gly Ile Val Val Cys Thr Ile Phe Met Leu Ala His Val Leu
                245                 250                 255

Glu Ser Thr Glu Phe Leu Thr Pro Asp Gly Glu Ser Gly Ala Ile Asp
            260                 265                 270

Asp Glu Trp Ala Ile Cys Gln Ile Arg Thr Thr Ala Asn Phe Ala Thr
        275                 280                 285

Asn Asn Pro Phe Trp Asn Trp Phe Cys Gly Gly Leu Asn His Gln Val
290                 295                 300

Thr His His Leu Phe Pro Asn Ile Cys His Ile His Tyr Pro Gln Leu
305                 310                 315                 320

Glu Asn Ile Ile Lys Asp Val Cys Gln Glu Phe Gly Val Glu Tyr Lys
                325                 330                 335

Val Tyr Pro Thr Phe Lys Ala Ala Ile Ala Ser Asn Tyr Arg Trp Leu
            340                 345                 350

Glu Ala Met Gly Lys Ala Ser
        355
```

(2) INFORMATION FOR SEQ ID NO:7:

(i) SEQUENCE CHARACTERISTICS:
        (A) LENGTH: 365 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

```
Met Thr Ser Thr Thr Ser Lys Val Thr Phe Gly Lys Ser Ile Gly Phe
1               5                   10                  15

Arg Lys Glu Leu Asn Arg Arg Val Asn Ala Tyr Leu Glu Ala Glu Asn
            20                  25                  30

Ile Ser Pro Arg Asp Asn Pro Met Tyr Leu Lys Thr Ala Ile Ile
        35                  40                  45

Leu Ala Trp Val Val Ser Ala Trp Thr Phe Val Phe Gly Pro Asp
50                  55                  60

Val Leu Trp Met Lys Leu Leu Gly Cys Ile Val Leu Gly Phe Gly Val
65                  70                  75                  80

Ser Ala Val Gly Phe Asn Ile Ser His Asp Gly Asn His Gly Tyr
                85                  90                  95

Ser Lys Tyr Gln Trp Val Asn Tyr Leu Ser Gly Leu Thr His Asp Ala
            100                 105                 110

Ile Gly Val Ser Ser Tyr Leu Trp Lys Phe Arg His Asn Val Leu His
            115                 120                 125

His Thr Tyr Thr Asn Ile Leu Gly His Asp Val Glu Ile His Gly Asp
130                 135                 140

Glu Leu Val Arg Met Ser Pro Ser Met Glu Tyr Arg Trp Tyr His Arg
145                 150                 155                 160

Tyr Gln His Trp Phe Ile Trp Phe Val Tyr Pro Phe Ile Pro Tyr Tyr
                165                 170                 175

Trp Ser Ile Ala Asp Val Gln Thr Met Leu Phe Lys Arg Gln Tyr His
            180                 185                 190

Asp His Glu Ile Pro Ser Pro Thr Trp Val Asp Ile Ala Thr Leu Leu
            195                 200                 205

Ala Phe Lys Ala Phe Gly Val Ala Val Phe Leu Ile Ile Pro Ile Ala
210                 215                 220

Val Gly Tyr Ser Pro Leu Glu Ala Val Ile Gly Ala Ser Ile Val Tyr
225                 230                 235                 240

Met Thr His Gly Leu Val Ala Cys Val Val Phe Met Leu Ala His Val
                245                 250                 255

Ile Glu Pro Ala Glu Phe Leu Asp Pro Asp Asn Leu His Ile Asp Asp
            260                 265                 270

Glu Trp Ala Ile Ala Gln Val Lys Thr Val Asp Phe Ala Pro Asn
            275                 280                 285

Asn Thr Ile Ile Asn Trp Tyr Val Gly Gly Leu Asn Tyr Gln Thr Val
            290                 295                 300

His His Leu Phe Pro His Ile Cys His Ile His Tyr Pro Lys Ile Ala
305                 310                 315                 320

Pro Ile Leu Ala Glu Val Cys Glu Glu Phe Gly Val Asn Tyr Ala Val
                325                 330                 335

His Gln Thr Phe Phe Gly Ala Leu Ala Ala Asn Tyr Ser Trp Leu Lys
            340                 345                 350

Lys Met Ser Ile Asn Pro Glu Thr Lys Ala Ile Glu Gln
```

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(ix) FEATURE:
        (A) NAME/KEY: misc_feature
        (B) LOCATION: 21
        (D) OTHER INFORMATION: /number= 1
            /note= "N=Inosine or Cytosine"

(ix) FEATURE:
        (A) NAME/KEY: misc_feature
        (B) LOCATION: 27
        (D) OTHER INFORMATION: /number= 2
            /note= "N=Inosine or Cytosine"

(xi) SEQUENCE DESCRIPTION: SEQ ID NO:8:

CUACUACUAC UACAYCAYAC NTAYACNAAY AT                    32

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(ix) FEATURE:
        (A) NAME/KEY: misc_feature
        (B) LOCATION: 13
        (D) OTHER INFORMATION: /number= 1
            /note= "N=Inosine or Cytosine"

(ix) FEATURE:
        (A) NAME/KEY: misc_feature
        (B) LOCATION: 19
        (D) OTHER INFORMATION: /number= 2
            /note= "N=Inosine or Cytosine"

(xi) SEQUENCE DESCRIPTION: SEQ ID NO:9:

CAUCAUCAUC AUNGGRAANA RRTGRTG                        27

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

CCAAGCTTCT GCAGGAGCTC TTTTTTTTTT TTTTT                 35

(2) INFORMATION FOR SEQ ID NO:11:

(i) SEQUENCE CHARACTERISTICS:
        (A) LENGTH: 5 amino acids
        (B) TYPE: amino acid

```
            (C) STRANDEDNESS: Not Relevant
            (D) TOPOLOGY: linear (ii) MOLECULE TYPE: peptide (xi) SEQUENCE DESCRIPTION: SEQ ID NO:11:

His Xaa Xaa His His
1               5

(2) INFORMATION FOR SEQ ID NO:12:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:12:

Gln Xaa Xaa His His
1               5
```

METHODS AND COMPOSITIONS FOR SYNTHESIS OF LONG CHAIN POLYUNSATURATED FATTY ACIDS

This is a divisional of application Ser. No. 08/833,610, filed Apr. 11, 1997, now U.S. Pat. No. 5,972,664.

FIELD OF THE INVENTION

This invention relates to modulating levels of enzymes and/or enzyme components relating to production of long chain poly-unsaturated fatty acids (PUFAs) in a microorganism or animal. The invention is exemplified by the production of arachidonic acid in yeast.

BACKGROUND

Two main families of poly-unsaturated fatty acids (PUFAs) are the ω3 fatty acids, exemplified by eicosapentaenoic acid (EPA), and the ω6 fatty acids, exemplified by arachidonic acid (ARA). PUFAs are important components of the plasma membrane of the cell, where they may be found in such forms as phospholipids and triglycerides. PUFAs are necessary for proper development, particularly in the developing infant brain, and for tissue formation and repair. PUFAs also serve as precursors to other molecules of importance in human beings and animals, including the prostacyclins, eicosanoids, leukotrienes and prostaglandins.

Four major long chain PUFAs of importance include docosahexaenoic acid (DHA) and EPA, which are primarily found in different types of fish oil, gamma-linolenic acid (GLA), which is found in the seeds of a number of plants, including evening primrose (*Oenothera biennis*), borage (*Borago officinalis*) and black currants (*Ribes nigrum*), and stearidonic acid (SDA), which is found in marine oils and plant seeds. Both GLA and another important long chain PUFA, arachidonic acid (ARA), are found in filamentous fungi. ARA can be purified from animal tissues including liver and adrenal gland. GLA, ARA, EPA and SDA are themselves, or are dietary precursors to, important long chain fatty acids involved in prostaglandin synthesis, in treatment of heart disease, and in development of brain tissue.

Several disorders respond to treatment with fatty acids. Supplementation with PUFAs has been shown to reduce the rate of restenosis after angioplasty. Fish oil supplements have been shown to improve symptoms of inflammation and rheumatoid arthritis, and PUFAs have been suggested as treatments for asthma and psoriasis. Evidence indicates that PUFAs may be involved in calcium metabolism, suggesting that PUFAs may be useful in the treatment or prevention of osteoporosis and of kidney or urinary tract stones.

PUFAs can be used in the treatment of cancer. Malignant cells have been shown to have altered fatty acid compositions; addition of fatty acids has been shown to slow their growth and cause cell death, and to increase their susceptibility to chemotherapeutic agents. GLA has been shown to cause reexpression on cancer cells of the E-cadherin cellular adhesion molecules, loss of which is associated with aggressive metastasis. Clinical testing of intravenous administration of the water soluble lithium salt of GLA to pancreatic cancer patients produced statistically significant increases in their survival. PUFA supplementation may also be usefull for treating cachexia associated with cancer.

PUFAs also can be used to treat diabetes (U.S. Pat. No. 4,826,877; Horrobin et al., Am. J. Clin. Nutr. Vol. 57 (Suppl.), 732S–737S). Altered fatty acid metabolism and composition has been demonstrated in diabetic animals. These alterations have been suggested to be involved in some of the long-term complications resulting from diabetes, including retinopathy, neuropathy, nephropathy and reproductive system damage. Primrose oil, which contains GLA, has been shown to prevent and reverse diabetic nerve damage.

Essential fatty acid deficiency has been suggested as being involved in eczema, and studies have shown beneficial effects on eczema from treatment with GLA. GLA has also been shown to reduce increases in blood pressure associated with stress, and to improve performance on arithmetic tests. GLA and DGLA have been shown to inhibit platelet aggregation, cause vasodilation, lower cholesterol levels and inhibit proliferation of vessel wall smooth muscle and fibrous tissue (Brenner et al., Adv. Exp. Med. Biol. Vol. 83, p. 85–101, 1976). Administration of GLA or DGLA, alone or in combination with EPA, has been shown to reduce or prevent gastrointestinal bleeding and other side effects caused by non-steroidal anti-inflammatory drugs (U.S. Pat. No. 4,666,701). GLA and DGLA have also been shown to prevent or treat endometriosis and premenstrual syndrome (U.S. Pat. No. 4,758,592) and to treat myalgic encephalomyelitis and chronic fatigue after viral infections (U.S. Pat. No. 5,116,871).

For DHA, a number of sources exist for commercial production including a variety of marine organisms, oils obtained from cold water marine fish, and egg yolk fractions. For ARA, microorganisms including the genera Mortierella, Entomophthora, Phytium and Porphyridium can be used for commercial production. Commercial sources of SDA include the genera Trichodesma and Echium. Commercial sources of GLA include evening primrose, black currants and borage. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFA. Natural sources also are subject to uncontrollable fluctuations in availability. Fish stocks may undergo natural variation or may be depleted by overfishing. Fish oils have unpleasant tastes and odors, which may be impossible to economically separate from the desired product, and can render such products unacceptable as food supplements. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large scale fermentation of organisms such as Mortierella is also expensive. Natural animal tissues contain low amounts of ARA and are difficult to process. Microorganisms such as Porphyridium and Mortierella are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Unpleasant tastes and odors of the supplements can make such regimens undesirable, and may inhibit compliance by the patient. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in ω3 fatty acids have an increased tendency to bleed (U.S. Pat. No. 4,874,603).

A number of enzymes are involved in PUFA biosynthesis. Linoleic acid (LA, 18:2 $\Delta^{9,12}$) is produced from oleic acid (18:1 $\Delta^9$) by a $\Delta$12-desaturase. GLA (18:3 $\Delta^{6,9,12}$) is produced from linoleic acid (LA, 18:2 $\Delta^{9,12}$) by a $\Delta$6-desaturase. ARA (20:4 $\Delta^{5,8,11,14}$) production from dihomo-gamma-linolenic acid (DGLA, 20:3 $\Delta^{8,11,14}$) is catalyzed by a $\Delta$5-desaturase. However, animals cannot desaturate beyond the $\Delta^9$ position and therefore cannot convert oleic acid (18:1 $\Delta^9$) into linoleic acid (18:2 $\Delta^{9,12}$). Likewise, α-linolenic acid (ALA, 18:3 $\Delta^{9,12,15}$) cannot be synthesized by mammals. Other eukaryotes, including fungi and plants, have enzymes which desaturate at positions $\Delta^{12}$ and $\Delta^{15}$. The major poly-unsaturated fatty acids of animals therefore are either derived from diet and/or from desaturation and elongation of linoleic acid (18:2 $\Delta^{9,12}$) or -linolenic acid (18:3 $\Delta^{9,12,15}$). Therefore it is of interest to obtain genetic material involved in PUFA biosynthesis from species that naturally produce these fatty acids and to express the isolated material in a microbial or animal system which can be manipulated to provide production of commercial quantities of one or more PUFAs. Thus there is a need for fatty acid desaturases, genes encoding them, and recombinant methods of producing them. A need further exists for oils containing higher relative proportions of and/or enriched in specific PUFAs. A need also exists for reliable economical methods of producing specific PUFAs.

Relevant Literature

Production of gamma-linolenic acid by a $\Delta$6-desaturase is described in U.S. Pat. No. 5,552,306. Production of 8,11-eicosadienoic acid using *Mortierella alpina* is disclosed in U.S. Pat. No. 5,376,541. Production of docosahexaenoic acid by dinoflagellates is described in U.S. Pat. No. 5,407,957. Cloning of a $\Delta$6-palmitoyl-acyl carrier protein desaturase is described in PCT publication WO 96/13591 and U.S. Pat. No. 5,614,400. Cloning of a $\Delta$6-desaturase from borage is described in PCT publication WO 96/21022. Cloning of $\Delta$9-desaturases is described in the published patent applications PCT WO 91/13972, EP 0 550 162 A1, EP 0 561 569 A2, EP 0 644 263 A2, and EP 0 736 598 A1, and in U.S. Pat. No. 5,057,419. Cloning of $\Delta$12-desaturases from various organisms is described in PCT publication WO 94/11516 and U.S. Pat. No. 5,443,974. Cloning of $\Delta$15-desaturases from various organisms is described in PCT publication WO 93/11245. All publications and U.S. patents or applications referred to herein are hereby incorporated in their entirety by reference.

SUMMARY OF THE INVENTION

Novel compositions and methods are provided for preparation of poly-unsaturated long chain fatty acids or PUFAs. The compositions include nucleic acids encoding a $\Delta$5-desaturase and/or polypeptides having $\Delta$5-desaturase activity, the polypeptides, and probes for isolating and detecting the same. The methods involve growing a host microorganism or animal which contains and expresses one or more transgenes encoding a $\Delta$5-desaturase and/or a polypeptide having $\Delta$5-desaturase activity. Expression of the desaturase polypeptide provides for a relative increase in $\Delta$5-desaturated PUFA, or metabolic progeny therefrom, as a result of altered concentrations of enzymes and substrates involved in PUFA biosynthesis. The invention finds use for example in the large scale production of PUFA containing oils which include, for example, ARA, EPA and/or DHA.

In a preferred embodiment, a nucleic acid sequence comprising a $\Delta$5-desaturase depicted in FIG. 3A–E (SEQ ID NO 1), a polypeptide encoded by the nucleic acid, and a purified or isolated polypeptide depicted in FIG. 3A–E (SEQ ID NO: 2), and an isolated nucleic acid encoding the polypeptide of FIG. 3A–E (SEQ ID NO: 2) are provided. Another embodiment of the invention is an isolated nucleic acid sequence which encodes a polypeptide, wherein said polypeptide desaturates a fatty acid molecule at carbon 5 from the carboxyl end of the molecule. The nucleic acid is preferably derived from a eukaryotic cell, such as a fungal cell, or a fungal cell of the genus Mortierella, or of the genus/species *Mortierella alpina*. Also preferred is an isolated nucleic acid comprising a sequence which anneals to a nucleotide sequence depicted in FIG. 3A–3E (SEQ ID NO: 1), and a nucleic acid which encodes an amino acid sequence depicted in FIG. 3A–E (SEQ ID NO: 2). In particular, the nucleic acid encodes an amino acid sequence depicted in FIG. 3A–E (SEQ ID NO: 2) which is selected from the group consisting of amino acid residues 30–38, 41–44, 171–175, 203–212, and 387–394. In an additional embodiment, the invention provides an isolated or purified polypeptide which desaturates a fatty acid molecules at carbon 5 from the carboxyl end of the molecule. Also provided is an isolated nucleic acid sequence which hybridizes to a nucleotide sequence depicted in FIG. 3A–E (SEQ ID NO 1), an isolated nucleic acid sequence having at least about 50% identity to FIG. 3A–E (SEQ ID NO 1).

The present invention further includes a nucleic acid construct comprising a nucleotide sequence depicted in a FIG. 3A–E (SEQ ID NO: 1) linked to a heterologous nucleic acid; a nucleic acid construct comprising a nucleotide sequence depicted in a FIG. 3A–E (SEQ ID NO: 1) operably linked to a promoter; and a nucleic acid construct comprising a nucleotide sequence depicted in a FIG. 3A–E (SEQ ID NO: 1) operably linked to a promoter which is functional in a microbial cell. In a preferred embodiment, the microbial cell is a yeast cell, and the nucleotide sequence is derived from a fungus, such as a fungus of the genus Mortierella, particularly a fungus of the species *Mortierella alpina*.

In another embodiment of the invention, a nucleic acid construct is provided which comprises a nucleotide sequence which encodes a polypeptide comprising an amino acid sequence which corresponds to or is complementary to an amino acid sequence depicted in FIG. 3A–E (SEQ ID NO: 2), wherein the nucleotide sequence is operably linked to a promoter which is functional in a host cell, and wherein the nucleotide sequence encodes a polypeptide which desaturates a fatty acid molecule at carbon 5 from the carboxyl end of a fatty acid molecule. Additionally, provided by the invention is a nucleic acid construct comprising a nucleotide sequence which encodes a functionally active $\Delta$5-desaturase, where the desaturase includes an amino acid sequence which corresponds to or is complementary to all of or a portion of an amino acid sequence depicted in a FIG. 3A–E (SEQ ID NO: 2), wherein the nucleotide sequence is operably linked to a promoter functional in a host cell.

The invention also includes a host cell comprising a nucleic construct of the invention. In a preferred embodiment, a recombinant host cell is provided which comprises at least one copy of a DNA sequence which encodes a functionally active *Mortierella alpina* fatty acid desaturase having an amino acid sequence as depicted in FIG. 3A–E (SEQ ID NO: 2), wherein the cell or an ancestor of the cell was transformed with a vector comprising said DNA sequence, and wherein the DNA sequence is operably linked to a promoter. The host cell is either eukaryotic or prokaryotic. Preferred eukaryotic host cells are those selected from the group consisting of a mammalian cell, an insect cell, a fungal cell, and an algae cell. Preferred mammalian cells include an avian cell, a fungal cell such as a yeast, and a marine algae cell. Preferred prokaryotic cells include those selected from the group consisting of a bacteria, a cyanobacteria, cells which contain a bacteriophage, and/or a virus. The DNA sequence of the recombinant host cell preferably contains promoter which is functional in the host cell.

The host cells of the invention which contain the DNA sequences of the invention are enriched for fatty acids, such as 20:3 fatty acids. In a preferred embodiment, the host cells are enriched for 20:4 fatty acids as compared to an untransformed host cell which is devoid of said DNA sequence, and/or enriched for 20:5 fatty acids compared to an untransformed host cell which is devoid of said DNA sequence. In yet another preferred embodiment, the invention provides a recombinant host cell which comprises a fatty acid selected from the group consisting of a dihomo-γ-linoleic acid, n-6 eicosatrienoic acid, 20:3n-6 acid and 20:3 (8,11,14) acid.

The present invention also includes method for production of arachidonic acid in a microbial cell culture, where the method comprises growing a microbial cell culture having a plurality of microbial cells which contain one or more nucleic acids encoding a polypeptide which converts dihomo-γ-linoleic acid to arachidonic acid, wherein the nucleic acid is operably linked to a promoter, under conditions whereby said one or more nucleic acids are expressed, whereby arachidonic acid is produced in the microbial cell culture. In several preferred embodiments of the invention, the polypeptide is an enzyme which desaturates a fatty acid molecule at carbon 5 from the carboxyl end of the fatty acid molecule; the nucleic acid is derived from a Mortierella sp.; and the substrate for said polypeptide is exogenously supplied. The microbial cells used in the methods can be either eukaryotic cells or prokaryotic cells. The preferred eukaryotic cells are those selected from the group consisting of a mammalian cell, an insect cell, a fungal cell, and an algae cell. Preferred mammalian cells include an avian cell, a preferred fungal cell is a yeast, and the preferred algae cell is a marine algae cell. The preferred prokaryotic cells include those selected from the group consisting of a bacteria, a cyanobacteria, cells which contain a bacteriophage, and/or a virus. The nucleic acid sequence encoding the polypeptide of the microbial cell preferably contains a promoter which is functional in the host cell which optionally is an inducible promoter for example by components of the culture broth. The preferred microbial cells used in the methods are yeast cells, such as Saccharomyces cells.

In another embodiment of the invention, a recombinant yeast cell is provided which converts greater than about 5% of 20:3 fatty acid substrate to a 20:4 fatty acid substrate Also provided is an oil comprising one or more PUFA. The amount of said one or more PUFAs is approximately 0.3–30% arachidonic acid (ARA), approximately 0.2–30% dihomo-γ-linoleic acid (DGLA), and approximately 0.2–30% γ-linoleic acid (GLA). A preferred oil of the invention is one in which the ratio of ARA:DGLA:GLA is approximately 1.0:19.0:30 to 6.0:1.0:0.2. Another preferred embodiment of the invention is a pharmaceutical composition comprising the oils in a pharmaceutically acceptable carrier. Further provided is a nutritional composition comprising the oils of the invention. The nutritional compositions of the invention preferably are administered to a mammalian host parenterally or internally. A preferred composition of the invention for internal consumption is an infant formula. In a preferred embodiment, the nutritional compositions of the invention are in a liquid form or a solid form.

The present invention also includes a method for desaturating a fatty acid, where the method comprises culturing a recombinant microbial cell of the invention under conditions suitable for expression of a polypeptide encoded by the nucleic acid, wherein the host cell further comprises a fatty acid substrate of the polypeptide. In a preferred embodiment, a fatty acid desaturated by the methods is provided, including an oil comprising the fatty acid.

BRIEF DESCRIPTION OF THE DRAWINGS

FIG. 3A–D shows the DNA sequence of the *Mortierella alpina* Δ5-desaturase (SEQ ID NO: 1)and the deduced amino acid sequence (SEQ ID NO: 2).

FIG. 4 shows the deduced amino acid sequence of the PCR fragment (SEQ ID NO: 3)(see Example 1)

FIGS. 5A, 5B and 5C show aligments of the protein sequence of the Δ5-desaturase (MA29, SEQ ID NO: 2) with Δ6-desaturases: MA524 (SEQ ID NO: 4), BorD6 (SEQ ID NO: 5), Sy6803D6 (SEQ ID NO: 6), and SplD6 (SEQ ID NO: 7)

FIG. 7A and 7B show the effect of inducer concentration on Δ5-desaturase expression in SC334.

FIG. 8A and 8B show the effect of induction temperature on Δ5-desaturase activity in SC334.

BRIEF DESCRIPTION OF THE SEQUENCE LISTINGS

Figure 1:
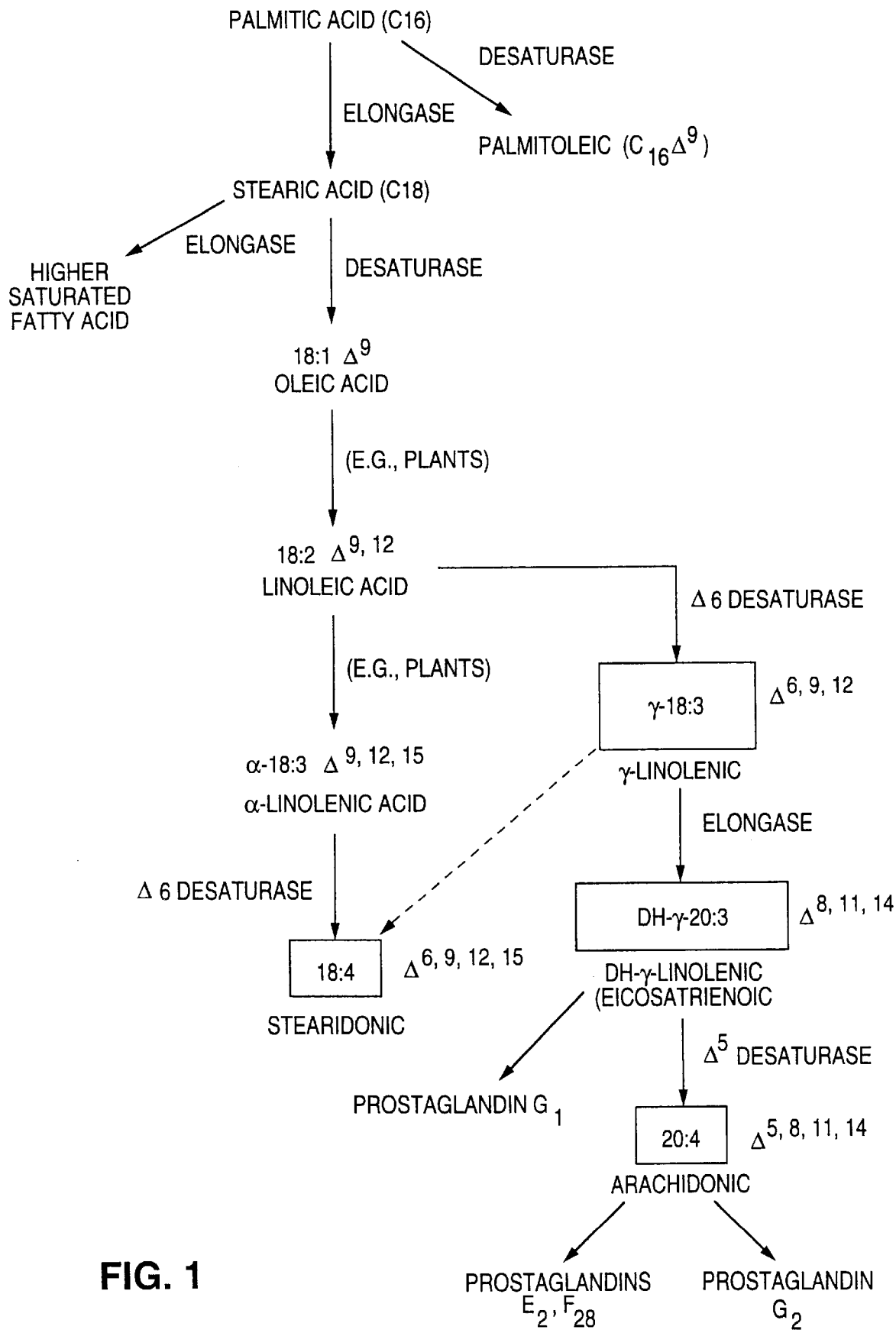
FIG. 1 shows possible pathways for the synthesis of arachidonic acid (20:4 $\Delta^{5,8,11,14}$) and stearidonic acid (18:4 $\Delta^{6,9,12,15}$) from palmitic acid ($C_{16}$) from a variety of organisms, including algae, Mortierella and humans. These PUFAs can serve as precursors to other molecules important for humans and other animals, including prostacyclins, leukotrienes, and prostaglandins, some of which are shown.

SEQ ID NO: 1 shows a DNA sequence of the *Mortierella alpina* Δ5-desaturase.

SEQ ID NO:2 shows an amino acid sequence of *Mortierella alpina* Δ5-desaturase.

DESCRIPTION OF THE PREFERRED EMBODIMENTS

In accordance with the subject invention, novel DNA sequences, DNA constructs, methods and compositions are provided which permit modification of the poly-unsaturated long chain fatty acid content of, for example, microbial cells or animals. Host cells are manipulated to express a sense or antisense transcript of a DNA encoding a polypeptide(s) which catalyzes the conversion of DGLA to ARA. The substrate(s) for the expressed enzyme may be produced by the host cell or may be exogenously supplied. To achieve expression, the transformed DNA is operably associated with transcriptional and translational initiation and termination regulatory regions that are functional in the host cell. Constructs comprising the gene to be expressed can provide for integration into the genome of the host cell or can autonomously replicate in the host cell. For production of ARA, the expression cassettes generally used include a cassette which provides for Δ5-desaturase activity, particularly in a host cell which produces or can take up DGLA. Production of ω6-type unsaturated fatty acids, such as ARA, is favored in a host microorganism or animal which is substantially free of ALA. The host is selected or obtained by removing or inhibiting activity of a Δ15- or ω3-type desaturase (see FIG. 2). The endogenous desaturase activity can be affected by providing an expression cassette for an antisense Δ15 or ω3 transcript, by disrupting a target Δ15- or ω3-desaturase gene through insertion, substitution and/or deletion of all or part of the target gene, or by adding a Δ15- or ω3-desaturase inhibitor. Production of LA also can be increased by providing expression cassettes for Δ9 and/or Δ12-desaturases where their respective enzymatic activities are limiting.

Microbial production of fatty acids has several advantages over purification from natural sources such as fish or plants. Many microbes are known with greatly simplified oil compositions compared with those of higher organisms, making purification of desired components easier. Microbial production is not subject to fluctuations caused by external variables such as weather and food supply. Microbially produced oil is substantially free of contamination by environmental pollutants. Additionally, microbes can provide PUFAs in particular forms which may have specific uses. For example, Spirulina can provide PUFAs predominantly at the first and third positions of triglycerides; digestion by pancreatic lipases preferentially releases fatty acids from these positions. Following human or animal ingestion of triglycerides derived from Spirulina, these PUFAs are released by pancreatic lipases as free fatty acids and thus are directly available, for example, for infant brain development. Additionally, microbial oil production can be manipulated by controlling culture conditions, notably by providing particular substrates for microbially expressed enzymes, or by addition of compounds which suppress undesired biochemical pathways. In addition to these advantages, production of fatty acids from recombinant microbes provides the ability to alter the naturally occurring microbial fatty acid profile by providing new synthetic pathways in the host or by suppressing undesired pathways, thereby increasing levels of desired PUFAs, or conjugated forms thereof, and decreasing levels of undesired PUFAs.

Production of fatty acids in animals also presents several advantages. Expression of desaturase genes in animals can produce greatly increased levels of desired PUFAs in animal tissues, making recovery from those tissues more economical. For example, where the desired PUFAs are expressed in the breast milk of animals, methods of isolating PUFAs from animal milk are well established. In addition to providing a source for purification of desired PUFAs, animal breast milk can be manipulated through expression of desaturase genes, either alone or in combination with other human genes, to provide animal milks with a PUFA composition substantially similar to human breast milk during the different stages of infant development. Humanized animal milks could serve as infant formulas where human nursing is impossible or undesired, or in cases of malnourishment or disease.

Depending upon the host cell, the availability of substrate, and the desired end product(s), several polypeptides, particularly desaturases, are of interest. By "desaturase" is intended a polypeptide which can desaturate one or more fatty acids to produce a mono- or poly-unsaturated fatty acid or precursor thereof of interest. Of particular interest are polypeptides which can catalyze the conversion of DGLA to produce ARA which includes enzymes which desaturate at the Δ5 position. By "polypeptide" is meant any chain of amino acids, regardless of length or post-translational modification, for example, glycosylation or phosphorylation. Considerations for choosing a specific polypeptide having desaturase activity include the pH optimum of the polypeptide, whether the polypeptide is a rate limiting enzyme or a component thereof, whether the desaturase used is essential for synthesis of a desired poly-unsaturated fatty acid, and/or co-factors required by the polypeptide. The expressed polypeptide preferably has parameters compatible with the biochemical environment of its location in the host cell. For example, the polypeptide may have to compete for substrate with other enzymes in the host cell. Analyses of the $K_m$ and specific activity of the polypeptide in question therefore are considered in determining the suitability of a given polypeptide for modifying PUFA production in a given host cell. The polypeptide used in a particular situation is one which can function under the conditions present in the intended host cell but otherwise can be any polypeptide having desaturase activity which has the desired characteristic of being capable of modifying the relative production of a desired PUFA.

For production of ARA, the DNA sequence used encodes a polypeptide having Δ5-desaturase activity. In particular instances, this can be coupled with an expression cassette which provides for production of a polypeptide having Δ6-desaturase activity and the host cell can optionally be depleted of any Δ15-desaturase activity present, for example by providing a transcription cassette for production of antisense sequences to the Δ15-desaturase transcription product, by disrupting the Δ15-desaturase gene, or by using a host cell which naturally has, or has been mutated to have, low Δ15-desaturase activity. Inhibition of undesired desaturase pathways also can be accomplished through the use of specific desaturase inhibitors such as those described in U.S. Pat. No. 4,778,630. The choice of combination of cassettes used can depend in part on the PUFA profile of the host cell. Where the host cell Δ5-desaturase activity is limiting, overexpression of Δ5-desaturase alone generally will be sufficient to provide for enhanced ARA production in the presence of an appropriate substrate such as DGLA. ARA production also can be increased by providing expression cassettes for Δ9- or Δ12-desaturase genes when the activities of those desaturases are limiting. A scheme for the synthesis of arachidonic acid (20:4 $\Delta^{5,8,11,14}$) from palmitic acid ($C_{16}$) is shown in FIG. 1. A key enzyme in this pathway is a Δ5-desaturase which converts DH-γ-linolenic acid (DGLA, eicosatrienoic acid) to ARA. Conversion of α-linolenic acid (ALA) to stearidonic acid by a Δ6-desaturase is also shown.

Figure 2:
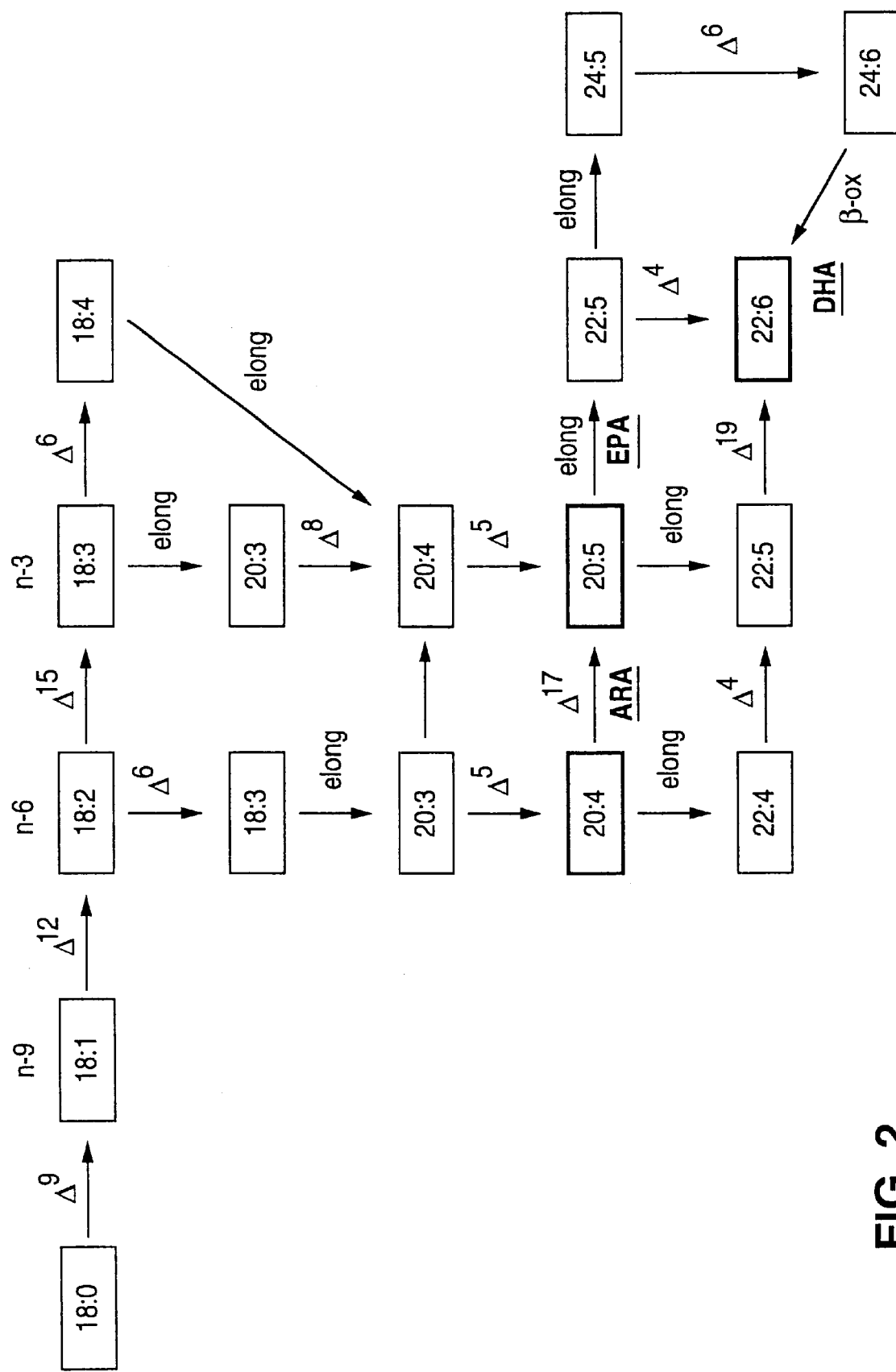
FIG. 2 shows possible pathways for production of PUFAs in addition to ARA, including EPA and DHA, for a variety of organisms.

Production of PUFAs in addition to ARA, including EPA and DHA is shown in FIG. 2.

As a source of polypeptides having desaturase activity and oligonucleotides encoding such polypeptides are organisms which produce a desired poly-unsaturated fatty acid. As an example, microorganisms having an ability to produce ARA can be used as a source of Δ5-desaturase activity. Such microorganisms include, for example, those belonging to the genera Mortierella, Conidiobolus, Pythium, Phytophathora, Penicillium, Porphyridium, Coidosporium, Mucor, Fusarium, Aspergillus, Rhodotorula, and Entomophthora. Within the genus Porphyridium, of particular interest is *Porphyridium cruentum*. Within the genus Mortierella, of particular interest are *Mortierella elongata, Mortierella exigua, Mortierella hygrophila, Mortierella ramanniana*, var. angulispora, and *Mortierella alpina*. Within the genus Mucor, of particular interest are *Mucor circinelloides* and *Mucor javanicus*.

DNAs encoding desired desaturases can be identified in a variety of ways. As an example, a source of the desired desaturase, for example genomic or cDNA libraries from Mortierella, is screened with detectable enzymatically- or chemically-synthesized probes, which can be made from DNA, RNA, or non-naturally occurring nucleotides, or mixtures thereof. Probes may be enzymatically synthesized from DNAs of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

For the most part, some or all of the coding sequence for the polypeptide having desaturase activity is from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring desaturase genes to produce a polypeptide having desaturase activity in vivo with more desirable physical and kinetic parameters for function in the host cell, such as a longer half-life or a higher rate of production of a desired polyunsaturated fatty acid.

Of particular interest is the *Mortierella alpina* Δ5-desaturase which has 446 amino acids; the amino acid sequence is shown in FIG. 3. The gene encoding the *Mortierella alpina* Δ5-desaturase can be expressed in transgenic microorganisms or animals to effect greater synthesis of ARA from DGLA. Other DNAs which are substantially identical to the *Mortierella alpina* Δ5-desaturase DNA, or which encode polypeptides which are substantially identical to the *Mortierella alpina* Δ5-desaturase polypeptide, also can be used. By substantially identical is intended an amino acid sequence or nucleic acid sequence exhibiting in order of increasing preference at least 60%, 80%, 90% or 95% homology to the *Mortierella alpina* Δ5-desaturase amino acid sequence or nucleic acid sequence encoding the amino acid sequence. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, and more preferably at least 75 nucleotides, and most preferably, 110 nucleotides. Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157: 105–132, 1982), or on the basis of the ability to assume similar polypeptide secondary structure (Chou and Fasman, *Adv. Enzymol.* 47:45–148, 1978).

Encompassed by the present invention are related desaturases from the same or other organisms. Such related desaturases include variants of the disclosed Δ5-desaturase naturally occurring within the same or different species of Mortierella, as well as homologues of the disclosed Δ5-desaturase from other species. Also included are desaturases which, although not substantially identical to the *Mortierella alpina* Δ5-desaturase, desaturate a fatty acid molecule at carbon 5 from the carboxyl end of a fatty acid molecule. Related desaturases can be identified by their ability to function substantially the same as the disclosed desaturases; that is, are still able to effectively convert DGLA to ARA. Related desaturases also can be identified by screening sequence databases for sequences homologous to the disclosed desaturase, by hybridization of a probe based on the disclosed desaturase to a library constructed from the source organism, or by RT-PCR using mRNA from the source organism and primers based on the disclosed desaturase.

The regions of a desaturase polypeptide important for desaturase activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them are within the scope of the present invention.

Once the DNA encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the DNA encoding the desaturase polypeptide. Expression of the polypeptide coding region can take place in vitro or in a host cell. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell.

In vitro expression can be accomplished, for example, by placing the coding region for the desaturase polypeptide in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The reaction mixture can then be assayed directly for the polypeptide, for example by determining its activity, or the synthesized polypeptide can be purified and then assayed.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source organism is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (U.S. Pat. No. 4,910,141).

When it is desirable to express more than one different gene, appropriate regulatory regions and expression methods, introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

As an example, where the host cell is a yeast, transcriptional and translational regions functional in yeast cells are provided, particularly from the host species. The transcriptional initiation regulatory regions can be obtained, for example from genes in the glycolytic pathway, such as alcohol dehydrogenase, glyceraldehyde-3-phosphate dehydrogenase (GPD), phosphoglucoisomerase, phosphoglycerate kinase, etc. or regulatable genes such as acid phosphatase, lactase, metallothionein, glucoamylase, etc. Any one of a number of regulatory sequences can be used in a particular situation, depending upon whether constitutive or induced transcription is desired, the particular efficiency of the promoter in conjunction with the open-reading frame of interest, the ability to join a strong promoter with a control region from a different promoter which allows for inducible transcription, ease of construction, and the like. Of particular interest are promoters which are activated in the presence of galactose. Galactose-inducible promoters (GAL1, GAL7, and GAL10) have been extensively utilized for high level and regulated expression of protein in yeast (Lue et al., *Mol. Cell. Biol. Vol.* 7, p. 3446, 1987; Johnston, *Microbiol. Rev.* Vol. 51, p. 458, 1987). Transcription from the GAL promoters is activated by the GAL4 protein, which binds to the promoter region and activates transcription when galactose is present. In the absence of galactose, the antagonist GAL80 binds to GAL4 and prevents GAL4 from activating transcription. Addition of galactose prevents GAL80 from inhibiting activation by GAL4.

Nucleotide sequences surrounding the translational initiation codon ATG have been found to affect expression in yeast cells. If the desired polypeptide is poorly expressed in yeast, the nucleotide sequences of exogenous genes can be modified to include an efficient yeast translation initiation sequence to obtain optimal gene expression. For expression in Saccharomyces, this can be done by site-directed mutagenesis of an inefficiently expressed gene by fusing it in-frame to an endogenous Saccharomyces gene, preferably a highly expressed gene, such as the lactase gene.

The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property. Preferably, the termination region is derived from a yeast gene, particularly Saccharomyces, Schizosaccharomyces, Candida or Kluyveromyces. The 3' regions of two mammalian genes, γ interferon and α2 interferon, are also known to function in yeast.

Constructs comprising the gene of interest may be introduced into a host cell by standard techniques. These techniques include transformation, protoplast fusion, lipofection, transfection, transduction, conjugation, infection, bolistic impact, electroporation, microinjection, scraping, or any other method which introduces the gene of interest into the host cell. Methods of transformation which are used include lithium acetate transformation (*Methods in Enzymology*, Vol. 194, p. 186–187, 1991). For convenience, a host cell which has been manipulated by any method to take up a DNA sequence or construct will be referred to as "transformed" or "recombinant" herein.

The subject host will have at least have one copy of the expression construct and may have two or more, depending upon whether the gene is integrated into the genome, amplified, or is present on an extrachromosomal element having multiple copy numbers. Where the subject host is a yeast, four principal types of yeast plasmid vectors can be used: Yeast Integrating plasmids (YIps), Yeast Replicating plasmids.(YRps), Yeast Centromere plasmids (YCps), and Yeast Episomal plasmids (YEps). YIps lack a yeast replication origin and must be propagated as integrated elements in the yeast genome. YRps have a chromosomally derived autonomously replicating sequence and are propagated as medium copy number (20 to 40), autonomously replicating, unstably segregating plasmids. YCps have both a replication origin and a centromere sequence and propagate as low copy number (10–20), autonomously replicating, stably segregating plasmids. YEps have an origin of replication from the yeast 2 $\mu$m plasmid and are propagated as high copy number, autonomously replicating, irregularly segregating plasmids. The presence of the plasmids in yeast can be ensured by maintaining selection for a marker on the plasmid. Of particular interest are the yeast vectors pYES2 (a YEp plasmid available from Invitrogen, confers uracil prototrophy and a GAL1 galactose-inducible promoter for expression), pRS425-pG1 (a YEp plasmid obtained from Dr. T. H. Chang, Ass. Professor of Molecular Genetics, Ohio State University, containing a constitutive GPD promoter and conferring leucine prototrophy), and pYX424 (a YEp plasmid having a constitutive TP1 promoter and conferring leucine prototrophy; Alber, T. and Kawasaki, G. (1982). *J. Mol. & Appl. Genetics* 1:419).

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host. Selection of a transformed host also can occur when the expressed marker protein can be detected, either directly or indirectly. The marker protein may be expressed alone or as a fusion to another protein. The marker protein can be detected by its enzymatic activity; for example β galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin and the amino glycoside G418 are of interest, as well as ability to grow on media lacking uracil, leucine, lysine or tryptophan.

The Δ5-desaturase-mediated production of PUFAs can be performed in either prokaryotic or eukaryotic host cells. Prokaryotic cells of interest include Eschericia, Bacillus, Lactobacillus, cyanobacteria and the like. Eukaryotic cells include mammalian cells such as those of lactating animals, avian cells such as of chickens, and other cells amenable to genetic manipulation including insect, fungal, and algae cells. The cells may be cultured or formed as part or all of a host organism including an animal. Viruses and bacteriophage also may be used with the cells in the production of PUFAs, particularly for gene transfer, cellular targeting and selection. In a preferred embodiment, the host is any microorganism or animal which produces DGLA and/or can assimilate exogenously supplied DGLA, and preferably produces large amounts of DGLA. Examples of host animals include mice, rats, rabbits, chickens, quail, turkeys, bovines, sheep, pigs, goats, yaks, etc., which are amenable to genetic manipulation and cloning for rapid expansion of the transgene expressing population. For animals, a Δ5-desaturase transgene can be adapted for expression in target organelles, tissues and body fluids through modification of the gene regulatory regions. Of particular interest is the production of PUFAs in the breast milk of the host animal.

Examples of host microorganisms include *Saccharomyces cerevisiae, Saccharomyces carlsbergensis*, or other yeast such as Candida, Kluyveromyces or other fungi, for example, filamentous fungi such as Aspergillus, Neurospora, Penicillium, etc. Desirable characteristics of a host microorganism are, for example, that it is genetically well characterized, can be used for high level expression of the product using ultra-high density fermentation, and is on the GRAS (generally recognized as safe) list since the proposed end product is intended for ingestion by humans. Of particular interest is use of a yeast, more particularly baker's yeast (*S. cerevisiae*), as a cell host in the subject invention. Strains of particular interest are SC334 (Mat αpep4-3 prb1–1122 ura3–52 leu2–3, 112 reg1–501 gal1; *Gene* 83:57–64, 1989, Hovland P. et al.), YTC34 (α ade2–101 his3Δ200 lys2–801 ura3–52; obtained from Dr. T. H. Chang, Ass. Professor of Molecular Genetics, Ohio State University), YTC41 (a/α ura3–52/ura3=52 lys2–801/lys2–801 ade2–101/ade2–101 trp1-Δ1/trp1-Δ1 his3Δ200/his3Δ200 leu2Δ1/leu2Δ1; obtained from Dr. T. H. Chang, Ass. Professor of Molecular Genetics, Ohio State University), BJ1995 (obtained from the Yeast Genetic Stock Centre, 1021 Donner Laboratory, Berkeley, Calif. 94720), INVSC1 (Mat α hiw3Δ1 leu2 trp1–289 ura3–52; obtained from Invitrogen, 1600 Faraday Ave., Carlsbad, Calif. 92008) and INVSC2 (Mat α his3Δ200 ura3–167; obtained from Invitrogen).

For producing PUFAs in avian species and cells, such as chickens, turkeys, quail and ducks, gene transfer can be performed by introducing a nucleic acid sequence encoding a Δ5-desaturase into the cells following procedures known in the art. If a transgenic animal is desired, pluripotent stem cells of embryos can be provided with a vector carrying a Δ5-desaturase encoding transgene and developed into adult animal (U.S. Pat. No. 5,162,215; Ono et al. (1996) *Comparative Biochemistry and Physiology A* 113(3): 287–292; WO 9612793; WO 9606160). In most cases, the transgene will be modified to express high levels of the desaturase in order to increase production of PUFAs. The transgene can be modified, for example, by providing transcriptional and/or translational regulatory regions that function in avian cells, such as promoters which direct expression in particular tissues and egg parts such as yolk. The gene regulatory regions can be obtained from a variety of sources, including chicken anemia or avian leukosis viruses or avian genes such as a chicken ovalbumin gene.

Production of PUFAs in insect cells can be conducted using baculovirus expression vectors harboring a Δ5-desaturase transgene. Baculovirus expression vectors are available from several commercial sources such as Clonetech. Methods for producing hybrid and transgenic strains of algae, such as marine algae, which contain and express a desaturase.transgene also are provided. For example, transgenic marine algae may be prepared as described in U.S. Pat. No. 5,426,040. As with the other expression systems described above, the timing, extent of expression and activity of the desaturase transgene can be regulated by fitting the polypeptide coding sequence with the appropriate transcriptional and translational regulatory regions selected for a particular use. Of particular interest are promoter regions which can be induced under preselected growth conditions. For example, introduction of temperature sensitive and/or metabolite responsive mutations into the desaturase transgene coding sequences, its regulatory regions, and/or the genome of cells into which the transgene is introduced can be used for this purpose.

The transformed host cell is grown under appropriate conditions adapted for a desired end result. For host cells grown in culture, the conditions are typically optimized to produce the greatest or most economical yield of PUFAs, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection. Microorganisms such as yeast, for example, are preferably grown using selected media of interest, which include yeast peptone broth (YPD) and minimal media (contains amino acids, yeast nitrogen base, and ammonium sulfate, and lacks a component for selection, for example uracil). Desirably, substrates to be added are first dissolved in ethanol. Where necessary, expression of the polypeptide of interest may be induced, for example by including or adding galactose to induce expression from a GAL promoter.

Expression in cells of a host animal can likewise be accomplished in a transient or stable manner. Transient expression can be accomplished via known methods, for example infection or lipofection, and can be repeated in order to maintain desired expression levels of the introduced construct (see Ebert, PCT publication WO 94/05782). Stable expression can be accomplished via integration of a construct into the host genome, resulting in a transgenic animal. The construct can be introduced, for example, by microinjection of the construct into the pronuclei of a fertilized egg, or by transfection, retroviral infection or other techniques whereby the construct is introduced into a cell line which may form or be incorporated into an adult animal (U.S. Pat. No. 4,873,191; U.S. Pat. No. 5,530,177; U.S. Pat. No. 5,565,362; U.S. Pat. No. 5,366,894; Wilmut et al. (1997) *Nature* 385:810). The recombinant eggs or embryos are transferred to a surrogate mother (U.S. Pat. No. 4,873,191; U.S. Pat. No. 5,530,177; U.S. Pat. No. 5,565,362; U.S. Pat. No. 5,366,894; Wilmut et al. (supra)).

After birth, transgenic animals are identified, for example, by the presence of an introduced marker gene, such as for coat color, or by PCR or Southern blotting from a blood, milk or tissue sample to detect the introduced construct, or by an immunological or enzymological assay to detect the expressed protein or the products produced therefrom (U.S. Pat. No. 4,873,191; U.S. Pat. No. 5,530,177; U.S. Pat. No. 5,565,362; U.S. Pat. No. 5,366,894; Wilmut et al. (supra)). The resulting transgenic animals may be entirely transgenic or may be mosaics, having the transgenes in only a subset of their cells. The advent of mammalian cloning, accomplished by fusing a nucleated cell with an enucleated egg, followed by transfer into a surrogate mother, presents the possibility of rapid, large-scale production upon obtaining a "founder" animal or cell comprising the introduced construct; prior to this, it was necessary for the transgene to be present in the germ line of the animal for propagation (Wilmut et al. (supra)).

Expression in a host animal presents certain efficiencies, particularly where the host is a domesticated animal. For production of PUFAs in a fluid readily obtainable from the host animal, such as milk, the desaturase transgene can be expressed in mammary cells from a female host, and the PUFA content of the host cells altered. The desaturase transgene can be adapted for expression so that it is retained in the mammary cells, or secreted into milk, to form the PUFA reaction products localized to the milk (PCT publication WO 95/24488). Expression can be targeted for expression in mammary tissue using specific regulatory sequences, such as those of bovine α-lactalbumin, α-casein, β-casein, γ-casein, κ-casein, β-lactoglobulin, or whey acidic protein, and may optionally include one or more introns and/or secretory signal sequences (U.S. Pat. No. 5,530,177; Rosen, U.S. Pat. No. 5,565,362; Clark et al., U.S. Pat. No. 5,366,894; Garner et al., PCT publication WO 95/23868). Expression of desaturase transgenes, or antisense desaturase transcripts, adapted in this manner can be used to alter the levels of specific PUFAs, or derivatives thereof, found in the animals milk. Additionally, the Δ5-desaturase transgene can be expressed either by itself or with other transgenes, in order to produce animal milk containing higher proportions of desired PUFAs or PUFA ratios and concentrations that resemble human breast milk (Prieto et al., PCT publication WO 95/24494).

The fatty acids desaturated in the Δ5 position may be found in the host microorganism or animal as free fatty acids or in conjugated forms such as acylglycerols, phospholipids, sulfolipids or glycolipids, and may be extracted from the host cell through a variety of means well-known in the art. Such means may include extraction with organic solvents, sonication, supercritical fluid extraction using for example carbon dioxide, and physical means such as presses, or combinations thereof. Of particular interest is extraction with methanol and chloroform. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Methods used include methylation of the fatty acids to produce methyl esters. Similarly, protecting groups may be removed at any step. Desirably, purification of fractions containing ARA, DHA and EPA may be accomplished by treatment with urea and/or fractional distillation.

There are several uses for the subject invention. Probes based on the DNAs of the present invention may find use in methods for isolating related molecules or in methods to detect organisms expressing desaturases. When used as probes, the DNAs or oligonucleotides must be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary. molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

PUFAs produced by recombinant means find applications in a wide variety of areas. Supplementation of humans or animals with PUFAs in various forms can result in increased levels not only of the added PUFAs, but of their metabolic progeny as well. For example, where the inherent Δ5-desaturase pathway is dysfunctional in an individual, treatment with ARA can result not only in increased levels of ARA, but also of downstream products of ARA such as prostaglandins (see FIG. 1). Complex regulatory mechanisms can make it desirable to combine various PUFAs, or to add different conjugates of PUFAs, in order to prevent, control or overcome such mechanisms to achieve the desired levels of specific PUFAs in an individual.

The PUFAs, or derivatives thereof, made by the disclosed method can be used as dietary substitutes, or supplements, particularly infant formulas, for patients undergoing intravenous feeding or for preventing or treating malnutrition. Typically, human breast milk has a fatty acid profile comprising from about 0.15% to about 0.36% as DHA, from about 0.03% to about 0.13 % as EPA, from about 0.30% to about 0.88% as ARA, from about 0.22% to about 0.67% as DGLA, and from about 0.27% to about 1.04% as GLA. Additionally, the predominant triglyceride in human milk has been reported to be 1,3-di-oleoyl-2-palmitoyl, with 2-palmitoyl glycerides reported as better absorbed than 2-oleoyl or 2-lineoyl glycerides (U.S. Pat. No. 4,876,107). Thus, fatty acids such as ARA, DGLA, GLA and/or EPA produced by the invention can be used to alter the composition of infant formulas to better replicate the PUFA composition of human breast milk. In particular, an oil composition for use in a pharmacologic or food supplement, particularly a breast milk substitute or supplement, will preferably comprise one or more of ARA, DGLA and GLA. More preferably the oil will comprise from about 0.3 to 30% ARA, from about 0.2 to 30% DGL, and from about 0.2 to about 30% GLA.

In addition to the concentration, the ratios of ARA, DGLA and GLA can be adapted for a particular given end use. When formulated as a breast milk supplement, an oil composition which contains two or more of ARA, DGLA and GLA will be provided in a ratio of about 1:19:30 to about 6:1:0.2, respectively. For example, the breast milk of animals can vary in ratios of ARA:DGLA:DGL ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to ARA can be used to precisely control the PUFA ratios. For example, a 5% to 10% conversion rate of DGLA to ARA can be used to produce an ARA to DGLA ratio of about 1:19, whereas a conversion rate of about 75% to 80% can be used to produce an ARA to DGLA ratio of about 6:1. Therefore, whether in a cell culture system or in a host animal, regulating the timing, extent and specificity of desaturase expression as described can be used to modulate the PUFA levels and ratios. Depending on the expression system used, e.g., cell culture or an animal expressing oil(s) in its milk, the oils also can be isolated and recombined in the desired concentrations and ratios. Amounts of oils providing these ratios of PUFA can be determined following standard protocols. PUFAs, or host cells containing them, also can be used as animal food supplements to alter an animal's tissue or milk fatty acid composition to one more desirable for human or animal consumption.

For dietary supplementation, the purified PUFAs, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

For pharmaceutical use (human or veterinary), the compositions are generally administered orally but can be administered by any route by which they may be successfully absorbed, e.g., parenterally (i.e. subcutaneously, intramuscularly or intravenously), rectally or vaginally or topically, for example, as a skin ointment or lotion. The PUFAs of the present invention may be administered alone or in combination with a pharmaceutically acceptable carrier or excipient. Where available, gelatin capsules are the preferred form of oral administration. Dietary supplementation as set forth above also can provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids. The typical normal adult plasma fatty acid profile comprises 6.64 to 9.46% of ARA, 1.45 to 3.11% of DGLA, and 0.02 to 0.08% of GLA. These PUFAs or their metabolic precursors can be administered, either alone or in mixtures with other PUFAs, to achieve a normal fatty acid profile in a patient. Where desired, the individual components of formulations may be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention; preferred is a composition having from about 1 to about 25 weight percent of the total PUFA composition as GLA (U.S. Pat. No. 5,196,198). Other vitamins, and particularly fat-soluble vitamins such as vitamin A, D, E and L-carnitine can optionally be included. Where desired, a preservative such as α tocopherol may be added, typically at about 0.1% by weight.

The following examples are presented by way of illustration, not of limitation.

EXAMPLES

Example 1

Isolation of a Δ5-Desaturase Nucleotide Sequence from *Mortierella alpina*

Example 2

Expression of *M. alpina* Δ5-desaturase Clones in Baker's Yeast

Example 3

Initial Optimization of Culture Conditions

Example 4

Distribution of PUFAs in Yeast Lipid Fractions

Example 5

Further Culture Optimization

Example 1

Isolation of a Δ5-Desaturase Nucleotide Sequence from *Mortierella Alpina*

*Motierella alpina* produces arachidonic acid (ARA, 20:4) from the precursor 20:3 by a Δ5-desaturase. A nucleotide sequence encoding the Δ5-desaturase from *Mortierella alpina* was obtained through PCR amplification using *M. alpina* $1^{st}$ strand cDNA and degenerate oligonucleotide primers corresponding to amino acid sequences conserved between Δ6-desaturases from Synechocystis and Spirulina. The procedure used was as follows:

Total RNA was isolated from a 3 day old PUFA-producing culture of *Mortierella alpina* using the protocol of Hoge et al. (1982) *Experimental Mycology* 6:225–232. The RNA was used to prepare double-stranded cDNA using BRL's lambda-ZipLox system, following the manufacturer's instructions. Several size fractions of the M alpina cDNA were packaged separately to yield libraries with different average-sized inserts. The "full-length" library contains approximately 3×10⁶ clones with an average insert size of 1.77 kb. The "sequencing-grade" library contains approximately 6×10⁵ clones with an average insert size of 1.1 kb.

5 μg of total RNA was reverse transcribed using BRL Superscript RTase, and the primer TSyn (5'-CCAAGCTTCTGCAGGAGCTCTTTTTTTTTTTTTT-3')(SEQ ID NO: 10). Degenerate oligonucleotides were designed to regions conserved between the two cyanobacterial Δ6-desaturase sequences. The specific primers used were D6DESAT-F3 (5'-CUACUACUACUACAYCAYA CNTAYACNAAYAT-3') (SEQ ID NO: 8) and D6DESAT-R3 (5'-CAUCAUCAUCAUNGGRAANARRTGRTG-3'), (SEQ ID NO: 9), where Y=C+T, R=A+G, and N=Tyrosine+C. PCR amplification was carried out in a 25 μl volume containing: template derived from 40 ng total RNA, 2 pM each primer, 200 µM each deoxyribonucleotide triphosphate, 60 mM Tris-Cl, pH 8.5, 15 MM (NH$_4$)$_2$SO$_4$, 2 mM MgCl$_2$. Samples were subjected to an initial denaturation step of 95 degrees (all temperatures Celsius) for 5 minutes, then held at 72 degrees while 0.2 U of Taq polymerase were added. PCR thermocycling conditions were as follows: 94 degrees for 1 min., 45 degrees for 1.5 min., 72 degrees for 2 min. PCR was continued for 35 cycles. PCR using these primers on the *M. alpina* first-strand cDNA produced a 550 bp reaction product. Comparison of the deduced amino acid sequence of the *M. alpina* PCR fragment revealed regions of homology with Δ6-desaturases (see FIG. 4). However, there was only about 28% identity over the region compared.

Figure 5A:
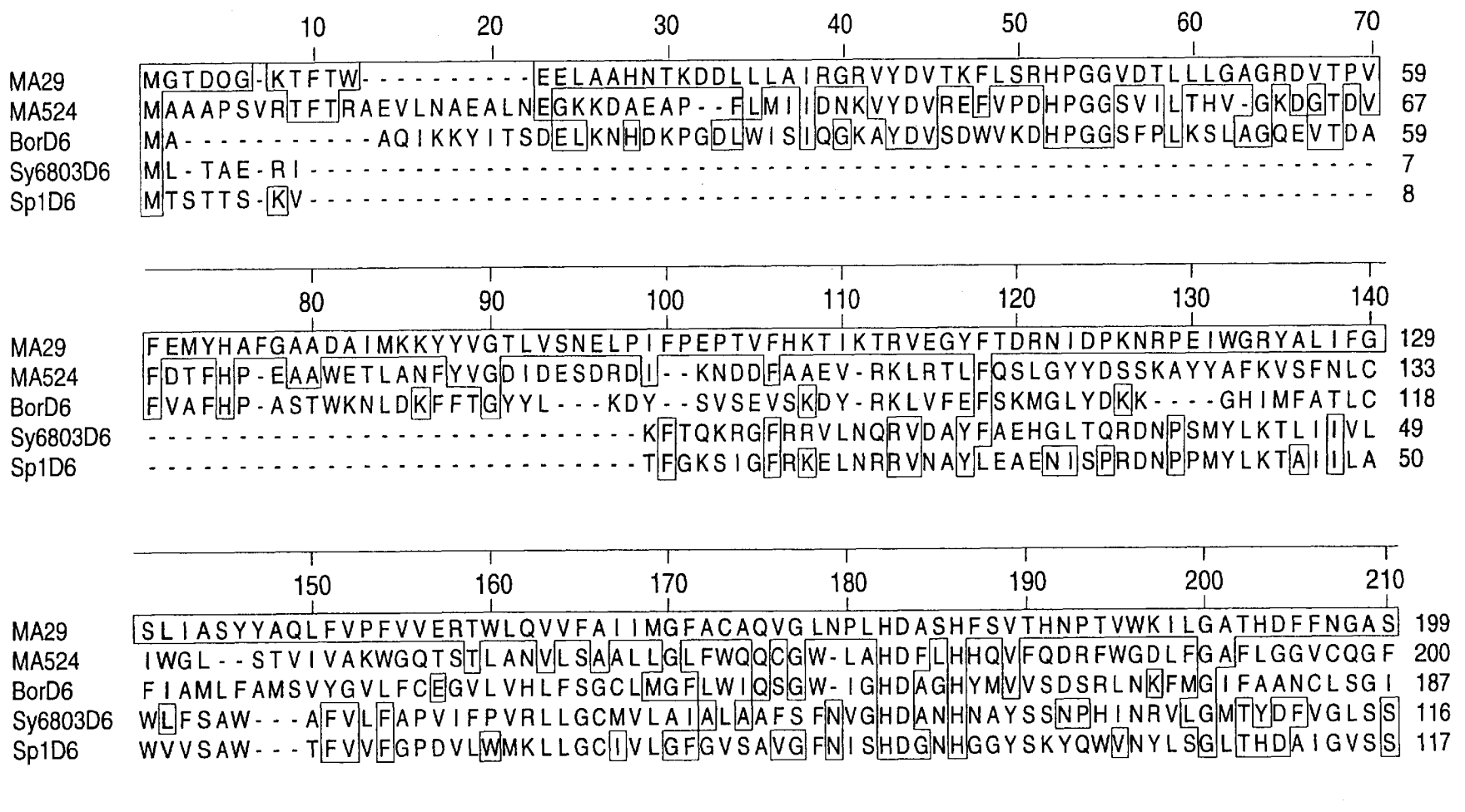
Figure 5B:
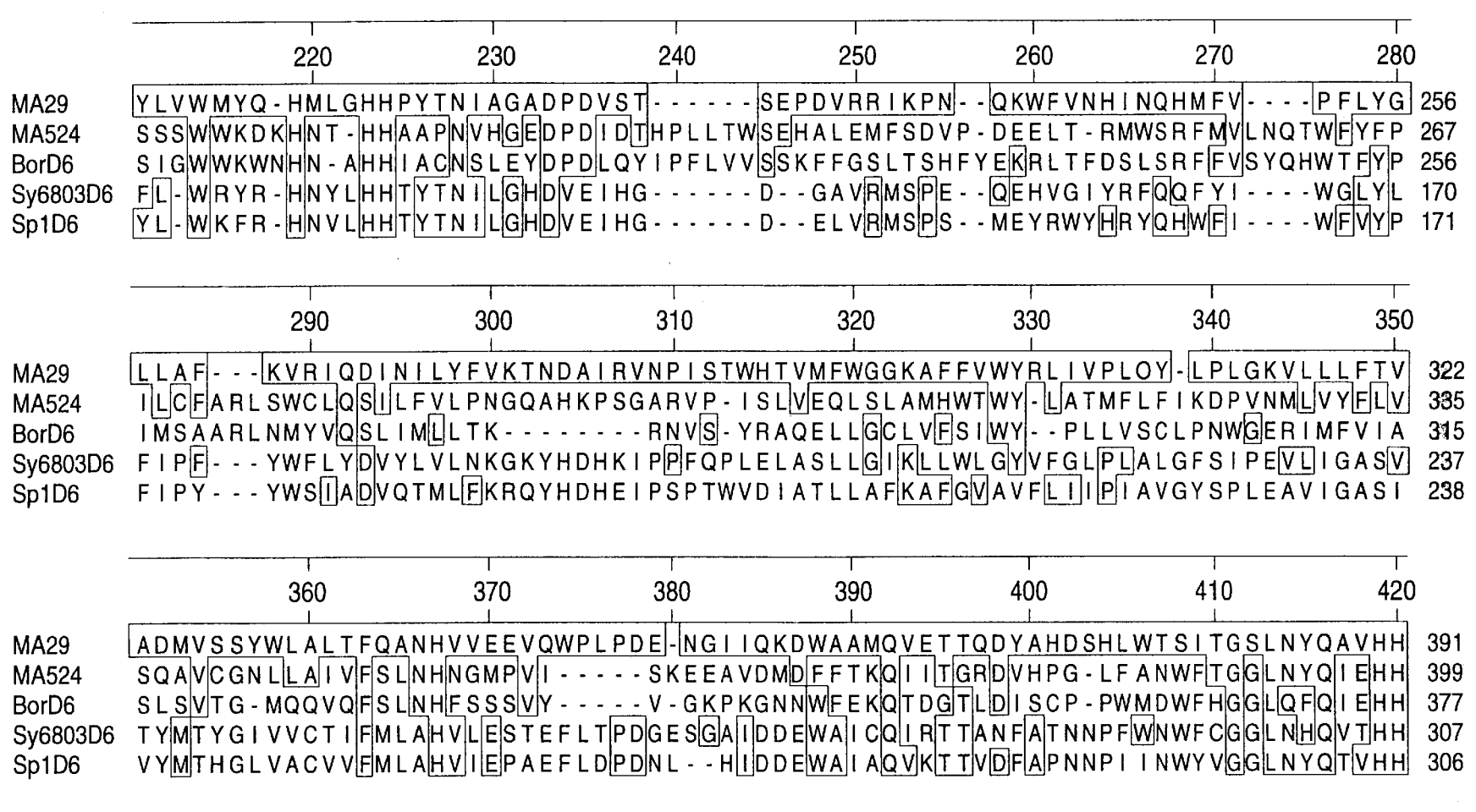

The PCR product was used as a probe to isolate corresponding cDNA clones from a *M. alpina* library. The longest cDNA clone, Ma29, was designated pCGN5521 and has been completely sequenced on both strands. The cDNA is contained as a 1481 bp insert in the vector pZL1 (Bethesda Research Laboratories) and, beginning with the first ATG, contains an open reading frame encoding 446 amino acids. The reading frame contains the sequence deduced from the PCR fragment. The sequence of the cDNA insert was found to contain regions of homology to Δ6-desaturases (see FIGS. 5A and 5B). For example, three conserved "histidine boxes" (that have been observed in all other membrane-bound desaturases (Okuley et al., (1994) The Plant Cell 6:147–158)) were found to be present in the Mortierella sequence at amino acid positions 171–175, 207–212, and 387–391 (see FIG. 3). However, the typical "HXXHH" (SEQ ID NO: 11) amino acid motif for the third histidine box for the Mortierella desaturase was found to be QXXHH (SEQ ID NO: 12). Surprisingly, the amino-terminus of the encoded protein, showed significant homology to cytochrome b5 proteins. Thus, the Mortierella cDNA clone appears to represent a fusion between a cytochrome b5 and a fatty acid desaturase. Since cytochrome b5 is believed to function as the electron donor for membrane-bound desaturase enzymes, it is possible that the N-terminal cytochrome b5 domain of this desaturase protein is involved in its function. This may be advantageous when expressing the desaturase in heterologous systems for PUFA production.

Example 2

Expression of *M. Alpina* Desaturase Clones in Baker's Yeast

Yeast Transformation

Lithium acetate transformation of yeast was performed according to standard protocols (*Methods in Enzymology*, Vol. 194, p. 186–187, 1991). Briefly, yeast were grown in YPD at 30° C. Cells were spun down, resuspended in TE, spun down again, resuspended in TE containing 100 mM lithium acetate, spun down again, and resuspended in TE/lithium acetate. The resuspended yeast were incubated at 30° C. for 60 minutes with shaking. Carrier DNA was added, and the yeast were aliquoted into tubes. Transforming DNA was added, and the tubes were incubated for 30 min. at 30° C. PEG solution (35% (w/v) PEG 4000, 100 mM lithium acetate, TE pH7.5) was added followed by a 50 min. incubation at 30° C. A 5 min. heat shock at 42° C. was performed, the cells were pelleted, washed with TE, pelleted again and resuspended in TE. The resuspended cells were then plated on selective media.

Desaturase Expression in Transformed Yeast

The cDNA clones from *Mortierella alpina* were screened for desaturase activity in baker's yeast. A canola Δ15-desaturase (obtained by PCR using 1$^{st}$ strand cDNA from *Brassica napus* cultivar 212/86 seeds using primers based on the published sequence (Arondel et al. *Science* 258:1353–1355)) was used as a positive control. The Δ15-desaturase gene and the gene from cDNA clone Ma29 was inserted into the expression vector pYES2 (Invitrogen), resulting in plasmids pCGR-2 and pCGR-4, respectively. These plasmids were transfected into *S. cerevisiae* yeast strain 334 and expressed after induction with galactose and in the presence of substrates that allowed detection of specific desaturase activity. The control strain was *S. cerevisiae* strain 334 containing the unaltered pYES2 vector. The substrates used, the products produced and the indicated desaturase activity were: DGLA (conversion to ARA would indicate Δ5-desaturase activity), linoleic acid (conversion to GLA would indicate Δ6-desaturase activity; conversion to ALA would indicate Δ15-desaturase activity), oleic acid (an endogenous substrate made by *S. cerevisiae*, conversion to linoleic acid would indicate Δ12-desaturase activity, which *S. cerevisiae* lacks), or ARA (conversion to EPA would indicate Δ17-desaturase activity). The results are provided in Table 1 below. The lipid fractions were extracted as follows: Cultures were grown for 48–52 hours at 15° C. Cells were pelleted by centrifugation, washed once with sterile ddH$_2$O, and repelleted. Pellets were vortexed with methanol; chloroform was added along with tritridecanoin (as an internal standard). The mixtures were incubated for at least one hour at room temperature or at 4° C. overnight. The chloroform layer was extracted and filtered through a Whatman filter with one gram of anhydrous sodium sulfate to remove particulates and residual water. The organic solvents were evaporated at 40° C. under a stream of nitrogen. The extracted lipids were then derivatized to fatty acid methyl esters (FAME) for gas chromatography analysis (GC) by adding 2 ml of 0.5 N potassium hydroxide in methanol to a closed tube. The samples were heated to 95° C. to 100° C. for 30 minutes and cooled to room temperature. Approximately 2 ml of 14% boron trifluoride in methanol was added and the heating repeated. After the extracted lipid mixture cooled, 2 ml of water and 1 ml of hexane were added to extract the FAME for analysis by GC. The percent conversion was calculated by dividing the product produced by the sum of (the product produced and the substrate added) and then multiplying by 100. To calculate the oleic acid percent conversion, as no substrate was added, the total linoleic acid produced was divided by the sum of (oleic acid and linoleic acid produced), then multiplying by 100.

TABLE 1

M. Alpina Desaturase Expression in Baker's Yeast

| CLONE | ENZYME ACTIVITY | % CONVERSION OF SUBSTRATE | |
|---|---|---|---|
| pCGR-2 | Δ6 | 0 | (18:2 to 18:3ω6) |
| (canola Δ15 | Δ15 | 16.3 | (18:2 to 18:3ω3) |
| desaturase) | Δ5 | 2.0 | (20:3 to 20:4ω6) |
|  | Δ17 | 2.8 | (20:4 to 20:5ω3) |
|  | Δ12 | 1.8 | (18:1 to 18:2ω6) |
| pCGR-4 | Δ6 | 0 | |
| (M. alpina | Δ15 | 0 | |
| Δ6-like, Ma29) | Δ5 | 15.3 | |
|  | Δ17 | 0.3 | |
|  | Δ12 | 3.3 | |

The Δ15-desaturase control clone exhibited 16.3% conversion of the substrate. The pCGR-4 clone expressing the Ma29 cDNA converted 15.3% of the 20:3 substrate to 20:4ω6, indicating that the gene encodes a Δ5-desaturase. The background (non-specific conversion of substrate) was between 0–3% in these cases. We also found substrate inhibition of the activity by using different concentrations of the substrate. When substrate was added to 100 μM, the percent conversion to product dropped compared to when substrate was added to 25 μM (see below). Additionally, by varying the DGLA substrate concentrations, between about 5 μM to about 200 μM percent conversion of DGLA to ARA ranged from about 5% to 75% with the *M. alpina* Δ5-desaturase.

These data show that desaturases with different substrate specificities can be expressed in a heterologous system and used to produce poly-unsaturated long chain fatty acids.

Table 2 represents fatty acids of interest as a percent of the total lipid extracted from the yeast host *S. cerevisiae* 334 with the indicated plasmid. No glucose was present in the growth media. Affinity gas chromatography was used to separate the respective lipids. GC/MS was employed to verify the identity product(s). The expected product for the *B. napus* Δ15-desaturase, α-linolenic acid, was detected when its substrate, linoleic acid, was added exogenously to the induced yeast culture. This finding demonstrates that yeast expression of a desaturase gene can produce functional enzyme and detectable amounts of product under the current growth conditions. Both exogenously added substrates were taken up by yeast, although slightly less of the longer chain PUFA, dihomo-γ-linolenic acid (20:3), was incorporated into yeast than linoleic acid (18:2) when either was added in free form to the induced yeast cultures. Arachidonic acid was detected as a novel PUFA in yeast when dihomo-γ-linolenic acid was added as the substrate to S. cerevisiae 334 (pCGR-4). This identifies pCGR-4 (MA29) as the Δ5-desaturase from *M. alpina*. Prior to this, no isolation and expression of a Δ5-desaturase from any source has been reported.

Example 3

Optimization of Culture Conditions

Table 3A shows the effect of exogenous free fatty acid substrate concentration on yeast uptake and conversion to fatty acid product as a percentage of the total yeast lipid extracted. In all instances, low amounts of exogenous substrate (1–10 μM) resulted in low fatty acid substrate uptake and product formation. Between 25 and 50 μM concentration of free fatty acid in the growth and induction media gave the highest percentage of fatty acid product formed, while the 100 μM concentration and subsequent high uptake into yeast appeared to decrease or inhibit the desaturase activity. The feedback inhibition of high fatty acid substrate concentration was well illustrated when the percent conversion rates of the respective fatty acid substrates to their respective products were compared in Table 3B. In all cases, 100 μM substrate concentration in the growth media decreased the percent conversion to product. The effect of media composition was also evident when glucose was present in the growth media for the Δ5-desaturase, since the percent of substrate uptake was decreased at 25 μM (Table 3A). However, the percent conversion by Δ5-desaturase increased by 18% and the percent product formed remained the same in the presence of glucose in the growth media.

TABLE 3A

Effect of Added Substrate on the Percentage of Incorporated Substrate and Product Formed in Yeast Extracts

| Plasmid in Yeast | pCGR-2 (Δ15) | pCGR-4 (Δ5) |
|---|---|---|
| substrate/product | 18:2/α–18:3 | 20:3/20:4 |
| 1 μM sub. | ND | 0.5/1.7 |
| 10 μM sub. | ND | 3.3/4 |
| 25 μM sub. | ND | 5.1/6.1 |
| 25 μM ◇ sub. | 36.6/7.2 ◇ | 9.3/5.4 ◇ |
| 50 μM sub. | 53.1/6.5 ◇ | ND |
| 100 μM sub. | 60.1/5.7 ◇ | 32.3/5.8 ◇ |

TABLE 2

Fatty Acid as a Percentage of Total Lipid Extracted from Yeast

| Plasmid in Yeast (enzyme) | 18:2 Incorporated | α-18:3 Produced | γ-18:3 Produced | 20:3 Incorporated | 20:4 Produced | 18:1* Present | 18:2 Produced |
|---|---|---|---|---|---|---|---|
| pYES2 (control) | 66.9 | 0 | 0 | 58.4 | 0 | 4 | 0 |
| pCGR-2 (Δ15) | 60.1 | 5.7 | 0 | 50.4 | 0 | 0.7 | 0 |
| pCGR-4 (Δ5) | 67 | 0 | 0 | 32.3 | 5.8 | 0.8 | 0 |

100 μM substrate added
*18:1 is an endogenous fatty acid in yeast
Key To Tables
18:1 = oleic acid
18:2 = linoleic acid
α-18:3 = α-linolenic acid
γ-18:3 = γ-linolenic acid
18:4 = stearidonic acid
20:3 = dihomo-γ-linolenic acid
20:4 = arachidonic acid

TABLE 3B

Effect of Substrate Concentration in Media on the Percent Conversion of Fatty Acid Substrate to Product in Yeast Extracts

| Plasmid in Yeast | pCGR-2 (Δ15) | pCGR-4 (Δ5) |
|---|---|---|
| substrate/product | 18:2→α-18:3 | 20:3→20:4 |
| 1 μM sub. | ND | 77.3 |
| 10 μM sub. | ND | 54.8 |
| 25 μM sub. | ND | 54.2 |
| 25 μM ◊ sub. | 16.4 | 36.7 |
| 50 μM sub. | 10.9 ◊ | ND |
| 100 μM sub. | 8.7 ◊ | 15.2 ◊ |

◊ no glucose in media
+Yeast peptone broth (YPD)
*18:1 is an endogenous yeast lipid
sub. is substrate concentration
ND (not done)

Table 4 shows the amount of fatty acid produced by a recombinant desaturase from induced yeast cultures when different amounts of free fatty acid substrate were used. Fatty acid weight was determined since the total amount of lipid varied dramatically when the growth conditions were changed, such as the presence of glucose in the yeast growth and induction media. To better determine the conditions when the recombinant desaturase would produce the most PUFA product, the quantity of individual fatty acids were examined. The absence of glucose reduced the amount of arachidonic acid produced by Δ5-desaturase by half. For Δ5-desaturase the amount of total yeast lipid was decreased by almost half in the absence of glucose.

TABLE 4

Fatty Acid Produced in μg from Yeast Extracts

| Plasmid in Yeast (enzyme) | pCGR-4 (Δ5) | pCGR-7 Δ12 |
|---|---|---|
| product | 20:4 | 18:2* |
| 1 μM sub. | 8.3 | ND |
| 10 μM sub. | 19.2 | ND |
| 25 μM sub. | 31.2 | 115.7 |
| 25 μM ◊ sub. | 16.8 | 39 ◊ |

◊ no glucose in media
sub. is substrate concentration
ND (not done)
*18:1, the substrate, is an endogenous yeast lipid

Example 4

Distribution of PUFAs in Yeast Lipid Fractions

Table 5 illustrates the uptake of free fatty acids and their new products formed in yeast lipids as distributed in the major lipid fractions. A total lipid extract was prepared as described above. The lipid extract was separated on TLC plates, and the fractions were identified by comparison to standards. The bands were collected by scraping, and internal standards were added. The fractions were then saponified and methylated as above, and subjected to gas chromatography. The gas chromatograph calculated the amount of fatty acid by comparison to a standard. It would appear that the substrates are accessible in the phospholipid form to the desaturases.

TABLE 5

Fatty Acid Distribution in Various Yeast Lipid Fractions μg

| Fatty acid fraction | Phospholipid | Diglyceride | Free Fatty Acid | Triglyceride | Cholesterol Ester |
|---|---|---|---|---|---|
| SC (pCGR-4) substrate 20:3 | 15.1 | 1.9 | 22.9 | 12.6 | 3.3 |
| SC (pCGR-4) product 20:4 | 42.6 | 0.9 | 6.8 | 4.9 | 0.4 |

SC = S. cerevisiae (plasmid)

Example 5

Further Culture Optimization

The growth and induction conditions for optimal activities of desaturases in *Saccharomyces cerevisiae* were evaluated. Various culture conditions that were manipulated for optimal activity were: I) induction temperature, ii) concentration of inducer, iii) timing of substrate addition, iv) concentration of substance, v) sugar source, vi) growth phase at induction. These studies were done using Δ5-desaturase gene from *Mortierella alpina* (MA 29). In addition, the effect of changing host strain on expression of the Δ5-desaturase gene was also determined.

Figure 6A:
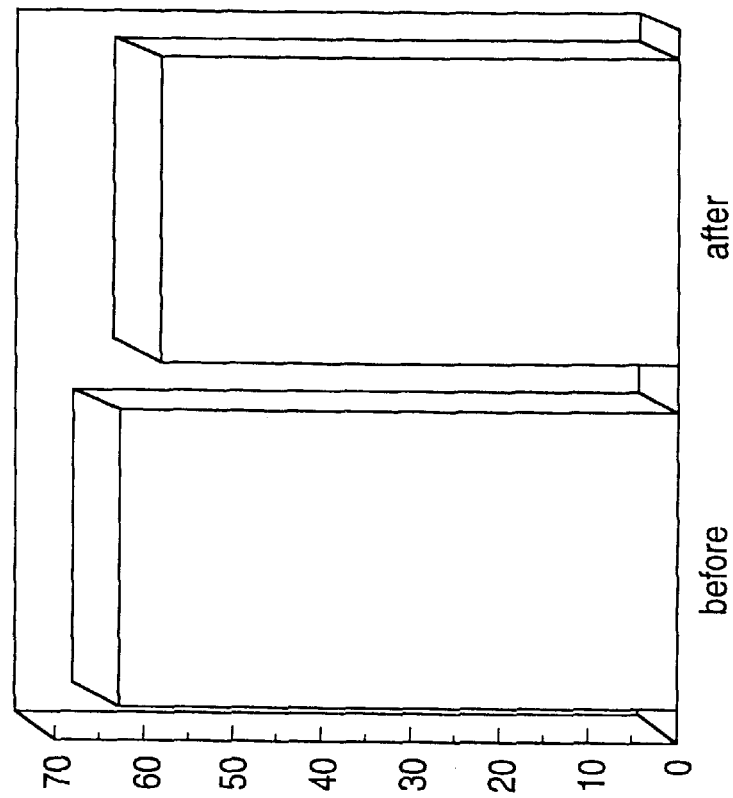
FIG. 6A and 6B show the effect of the timing of substrate addition relative to induction on conversion of substrate to product in SC334 containing the Δ5-desaturase gene.
Figure 6B:
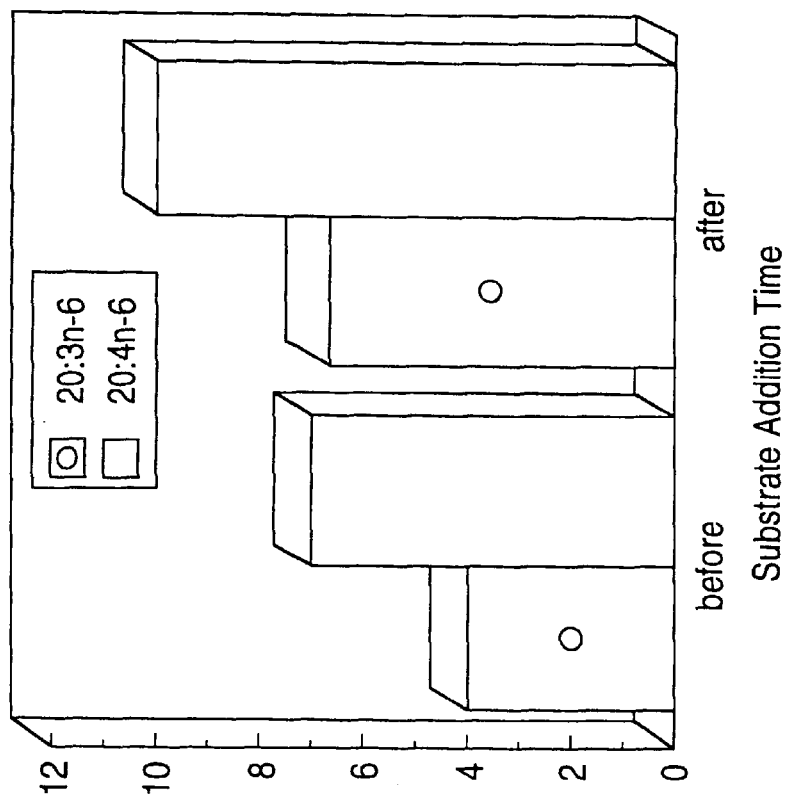

As described above, the best rate of conversion of substrate to ARA was observed at a substrate concentration of 1 μM, however, the percentage of ARA in the total fatty acids was highest at 25 μM substrate concentration. To determine if the substrate needed to be modified to a readily available form before it could be utilized by the desaturase, the substrate was added either 15 hours before induction or concomitant with inducer addition (indicated as after, in FIG. 6A). As it can be seen in FIG. 6A, addition of substrate before induction did not have a significant effect on the activity of Δ5-desaturase. In fact, addition of substrate along with the inducer was slightly better for expression/activity of Δ5-desaturase, as ARA levels in the total fatty acids were higher. However, the rate of conversion of substrate to product was slightly lower.

The effect of inducer concentration of expression/activity of Mortierella Δ5-desaturase was examined by inducing SC334/pCGR5 with 0.5 or 2% (w/v) of galactose. As shown in FIGS. 7A and 7B, expression of Δ5-desaturase was higher when induced with 0.5% galactose. Furthermore, rate of conversion of substrate to product was also better when SC334/pCGR5 was induced with 0.5% galactose vs 2% galactose.

To determine the effect of temperature on Δ5-desaturase activity, the SC334 host strain, transformed with pCGR5 (SC334/pCGR5) was grown and induced at 15° C., 25° C., 30° C. and 37° C. The quantity of ARA (20:4n6) produced in SC334/pCGR5 cultures, supplemental with substrate 20:3n6, was measured by fatty acid analysis. FIG. 8A depicts the quantity of 20:3n6 and 20:4n6, expressed as percentage of total fatty acids. FIG. 8B depicts the rate of conversion of substrate to product. Growth and induction of SC334/pCGR5 at 25° C., was the best for the expression of Δ5-desaturase as evidenced by the highest levels of arachidonic acid in the total fatty acids. Additionally the highest rate of conversion of substrate to product also occurred at 25° C. Growth and induction at 15° C. gave the lowest expression of ARA, whereas at 37° C. gave the lowest conversion of substrate to product.

Figures 9A, 9B:
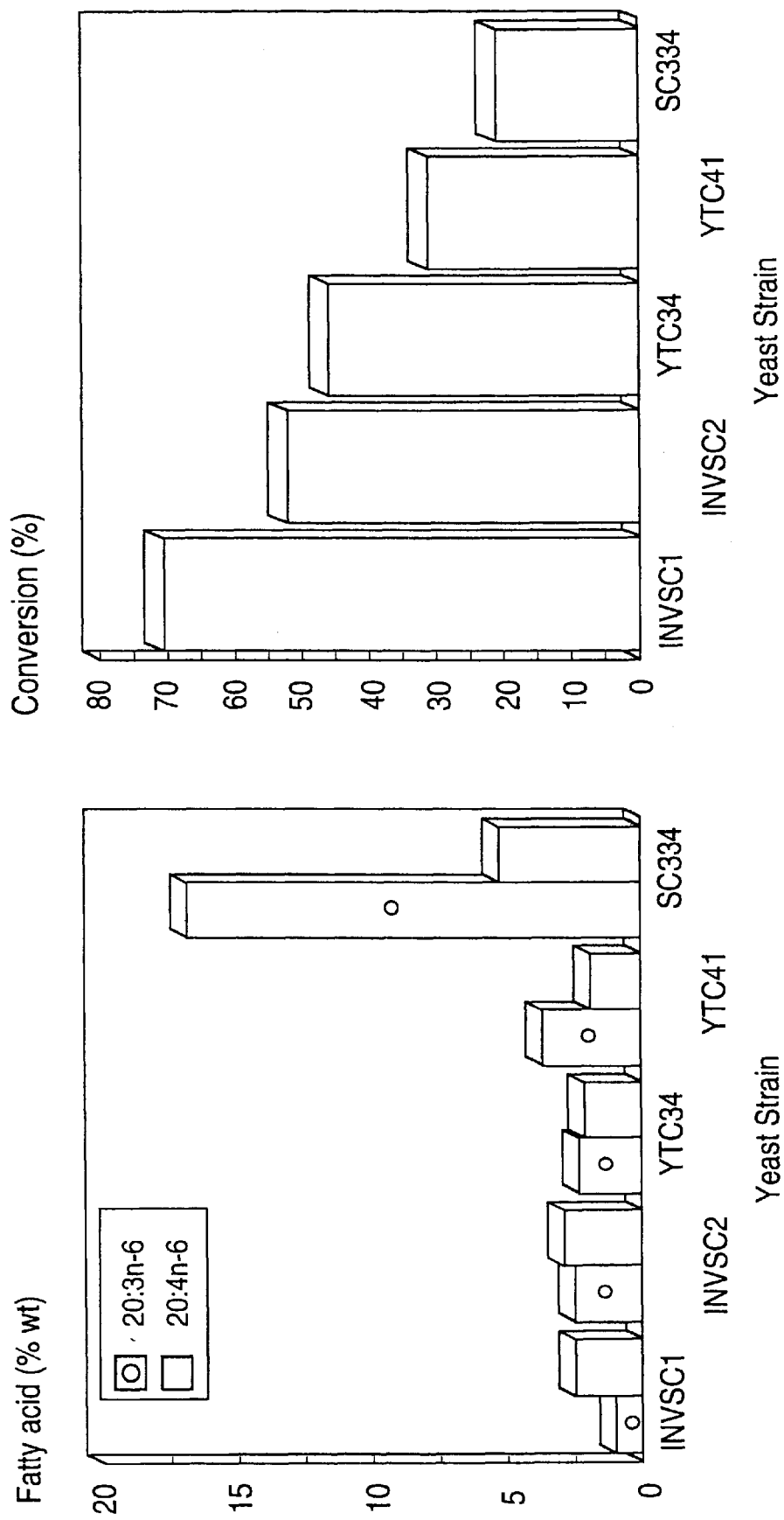
FIG. 9A and 9B shows the effect of host strain on the conversion of substrate to product in strains expressing the Δ5-desaturase gene at 15° C.
Figure 10B:
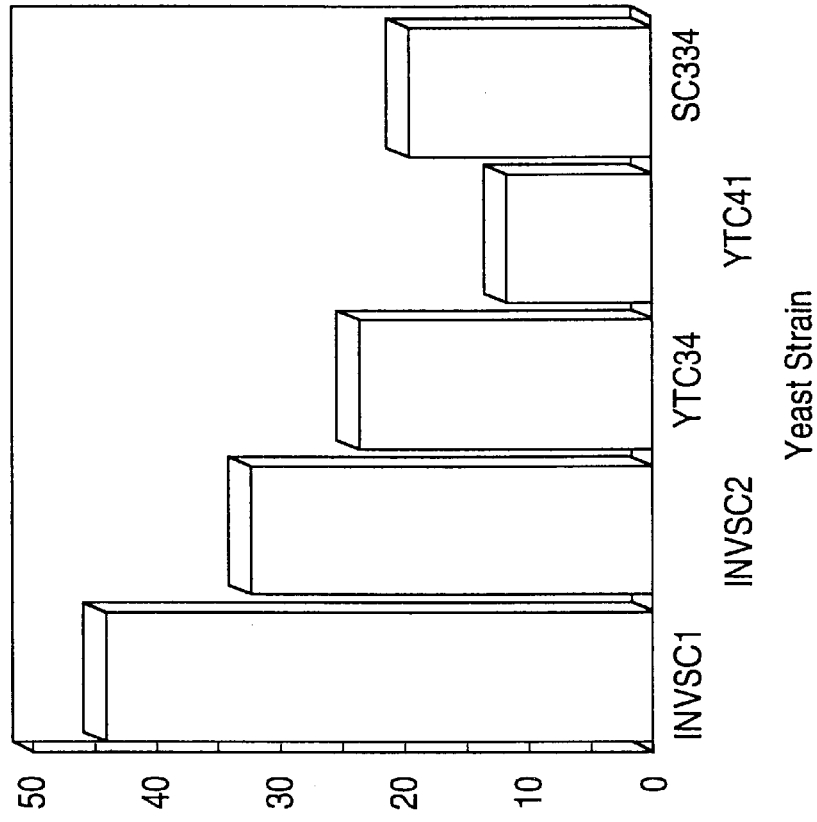
FIG. 10A and 10B shows the effect of host strain on the conversion of substrate to product in strains expressing the Δ5-desaturase gene at 30° C.
Figure 10A:
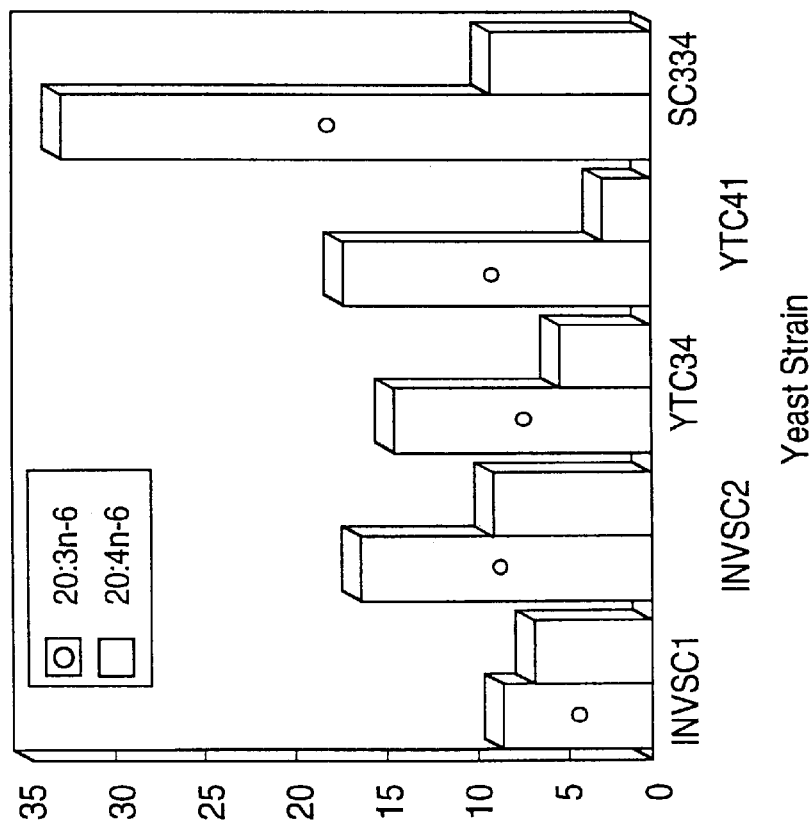

The effect of yeast strain on expression of the Δ5-desaturase gene was studied in 5 different host strains; INVSC1, INVSC2, YTC34, YTC41, and SC334, at 15° C. and 30° C. At 15° C., SC334 has the highest percentage of ARA in total fatty acids, suggesting higher activity of Δ5-desaturase in SC334. The rate of conversion of substrate to product, however is lowest in SC334 and highest in INVSC 1 (FIG. 9A and B). At 30° C., the highest percentage of product (ARA) in total fatty acids was observed in INVSC2, although the rate of conversion of substrate to product in INVSC2 was slightly lower than INVSC1 (FIG. 10A and B).

Figure 11:
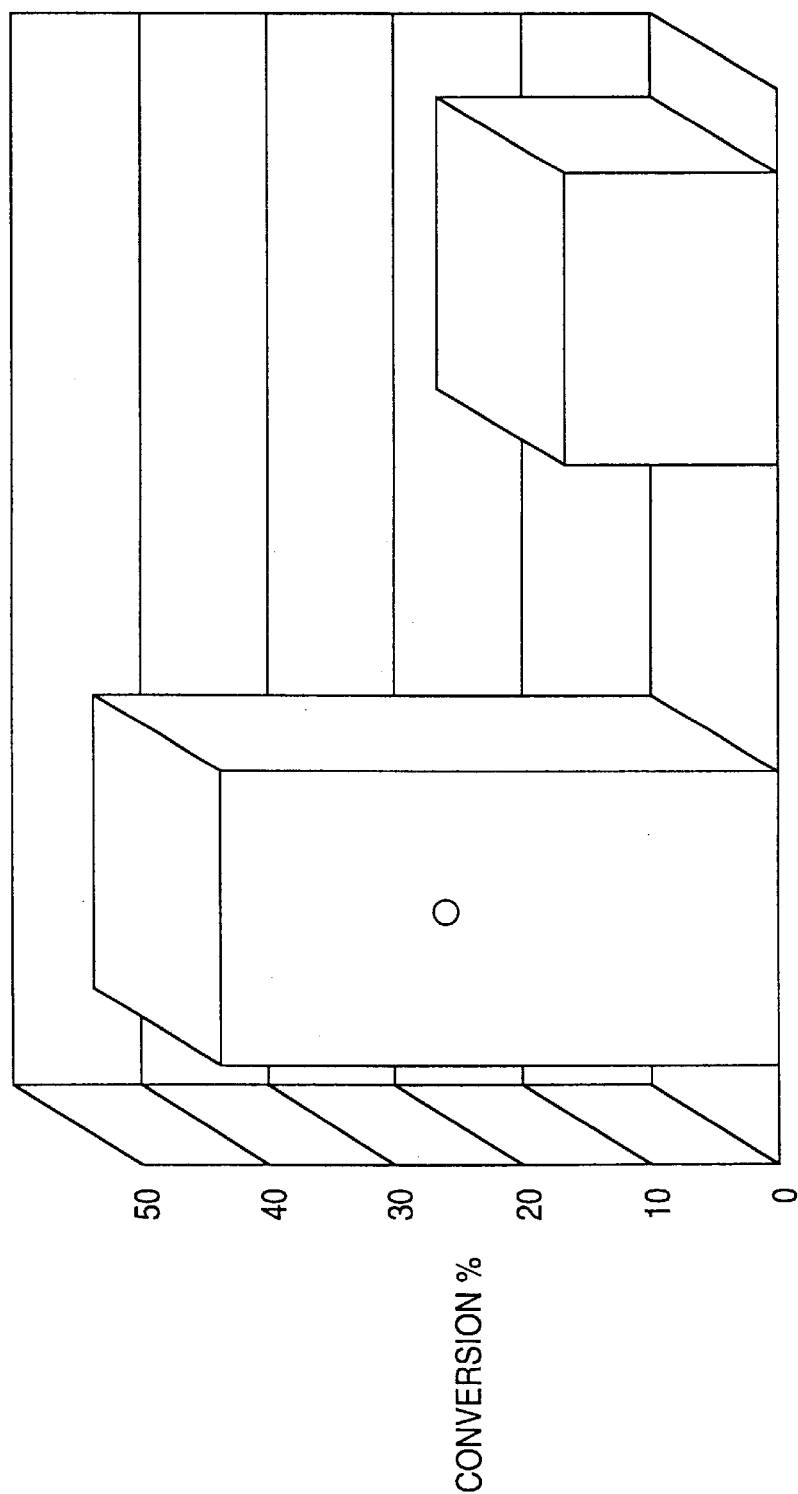
FIG. 11 shows the effect of a host strain expressing choline transferase as well as the Δ5-desaturase gene on the conversion of substrate to product.

ARA, the product of Δ5-desaturase, is stored in the phospholipid faction (Example 4). Therefore the quantity of ARA produced in yeast is limited by the amount that can be stored in the phospholipid fraction. If ARA could also be stored in other fractions such as the triglyceride fraction, the quantity of ARA produced in yeast might be increased. To test this hypothesis, the Δ5-desaturase gene was expressed in the yeast host strain DBY746 (obtained from the Yeast Genetic Stock Centre, 1021 Donner Laboratory, Berkeley, Calif. 94720. The genotype of strain DBY746 is Matα, his3-Δ1, leu2–3, leu2–112, ura3–32, trp1–289, gal). The DBY746 yeast strain has an endogenous gene for choline transferase. The presence of this enzyme might enable the DBY746 strain to convert excess phospholipids into triglycerides fraction. Results in FIG. 11 show no increase in the conversion of substrate to product as compared to SC334, which does not have the gene for choline transferase.

Figure 12B:
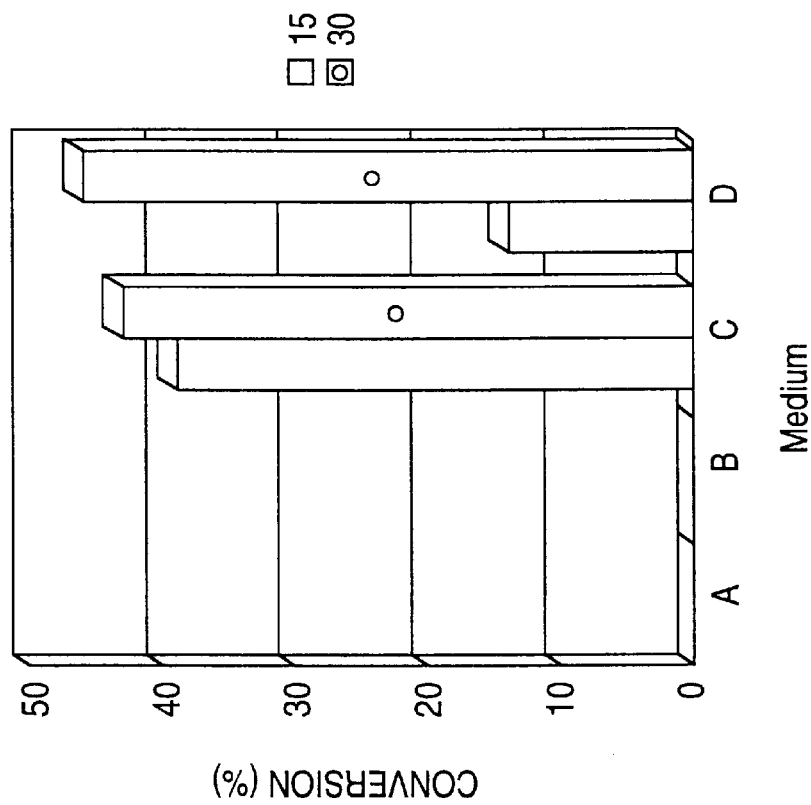
FIG. 12A and 12B show the effect of media composition and temperature on the conversion of substrate to product in two host strains expressing the Δ5-desaturase gene.
Figure 12A:
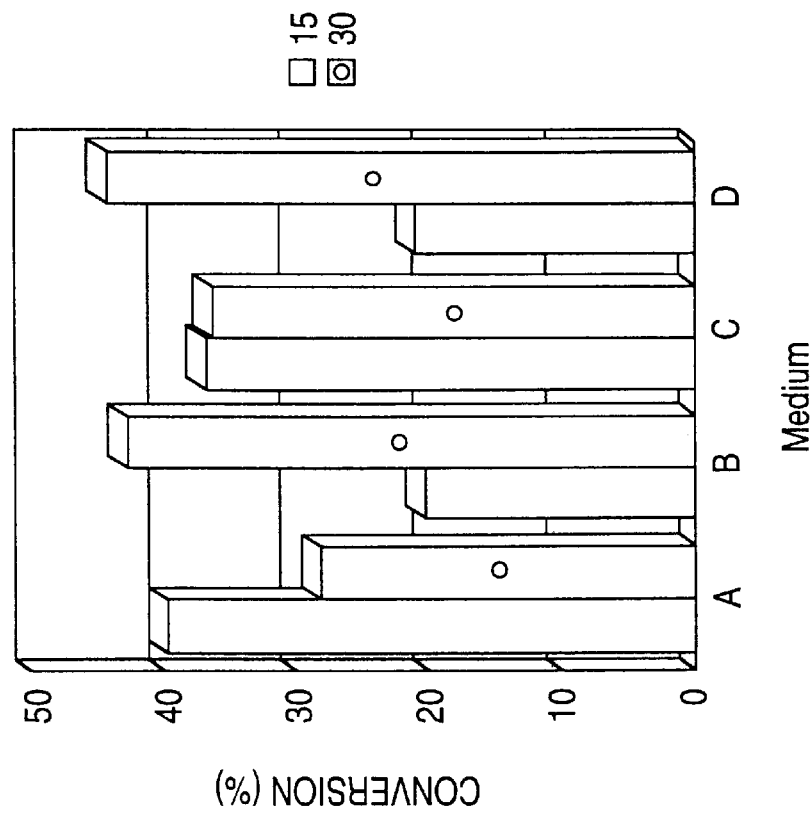

To study the effect of media on expression of Δ5-desaturase, pCGR4/SC334 was grown in four different media at two different temperatures (15° C. and 30°) and in two different host strains (SC334 and INVSC1). The composition of the media was as follows:

Media A: mm-Ura, +2% galactose+2% glucose.
Media B: mm-Ura, +20% galactose+2% Glucose+1M sorbitol (pH5.8)
Media C: mm-Ura, +2% galactose+2% raffinose
Media D: mm-Ura, +2% galactose+2% raffinose+1M sorbitol (pH5.8)
mm=minimal media Results show that the highest conversion rate of substrate to product at 15° C. in SC334 was observed in media A. The highest conversion rate overall for Δ5-desaturase in SC334 was at 30° in media D. The highest conversion rate of Δ5-desaturase in INVSC1 was also at 30° in media D (FIGS. 12A and 12B).

These data show that a DNA encoding a desaturase that can convert DGLA to ARA can be isolated from *Mortierella alpina* and can be expressed in a heterologous system and used to produce poly-unsaturated long chain fatty acids. Exemplified is the production of ARA from the precursor DGLA by expression of a Δ5-desaturase in yeast.

All publications and patent applications mentioned in this specification are indicative of the level of skill of those skilled in the art to which this invention pertains. All publications and patent applications are herein incorporated by reference to the same extent as if each individual publication or patent application was specifically and individually indicated as incorporated by reference.

The invention now being fully described, it will be apparent to one of ordinary skill in the art that many changes and modifications can be made thereto without departing from the spirit or scope of the appended claims.

What is claimed is:

1. A purified or isolated polypeptide encoded by the nucleic acid depicted in SEQ ID NO: 1.

2. A purified or isolated polypeptide comprising the amino acid sequence depicted in SEQ ID NO:2.

3. The polypeptide of claim 1, wherein said polypeptide is produced by expression of said nucleic acid in a host cell, wherein said nucleic acid is operably linked to a promoter functional in the host cell.

4. The polypeptide of claim 3 wherein said host cell is a yeast cell or an algae cell.

5. The polypeptide of claim 4 wherein said host cell is a yeast cell.

6. The polypeptide of claim 4 wherein said host cell is an algae cell.

7. A purified or isolated polypeptide encoded by a nucleic acid with at least 80% homology to the sequence depicted in SEQ ID NO: 1, wherein said polypeptide forms a monounsaturated bond between carbons 5 and 6 of a fatty acid as numbered from a carboxy terminus thereof.

8. The polypeptide of claim 7, wherein said polypeptide is encoded by a nucleic acid with at least 90% homology to the sequence depicted in SEQ ID NO: 1.

9. The polypeptide of claim 8, wherein said polypeptide is encoded by a nucleic acid with at least 95% homology to the sequence depicted in SEQ ID NO: 1.

10. A purified or isolated polypeptide, wherein said polypeptide has at least 80% homology to the sequence depicted in SEQ ID NO:2 and said polypeptide forms a monounsaturated bond between carbons 5 and 6 of a fatty acid as numbered from a carboxy terminus thereof.

11. The polypeptide of claim 10, wherein said polypeptide has at least 90% homology to the sequence depicted in SEQ ID NO:2.

12. The polypeptide of claim 11, wherein said polypeptide has at least 95% homology to the sequence depicted in SEQ ID NO:2.

13. A catalytically active deletion mutant of the polypeptide of claim 1, wherein the deletion mutant lacks at least one amino acid of said polypeptide, wherein said deletion mutant forms a monounsaturated bond between carbons 5 and 6 of a fatty acid as numbered from a caiboxy terminus thereof.

14. A catalytically active deletion mutant of the potypeptide of claim 2, wherein the deletion mutant lacks at least one amino acid of said polypeptide, wherein said deletion mutant forms a monounsaturated bond between carbons 5 and 6 of a fatty acid as numbered from a carboxy terminus thereof.

15. A catalytically active deletion mutant of the polypeptide of claim 7, wherein the deletion mutant lacks at least one amino acid of said polypeptide.

16. A catalytically active deletion mutant of the polypeptide of claim 8, wherein the deletion mutant lacks at least one amino acid of said polypeptide.

17. A catalytically active deletion mutant of the polypeptide of claim 9, wherein the deletion mutant lacks at least one amino acid of said polypeptide.

18. A catalytically active deletion mutant of the polypeptide of claim 10, wherein the deletion mutant lacks at least one amino acid of said polypeptide.

19. The polypeptide of claim 5 wherein said yeast cell is a Saccharomyces cell.

20. The polypeptide of claim 6 wherein said algae cell is a marine algae cell.

21. The polypeptide of claim 7 wherein the sequence of said polypeptide comprises a sequence selected from the group consisting of residues 30–38, 41–44, 171–175, 203–212 and 387–394 of SEQ ID NO:2.

22. The polyeptide of claim 10 wherein the sequence of said polypeptide comprises a sequence selected from the group consisting of residues 30–38, 41–44, 171–175, 203–212 and 387–394 of SEQ ID NO:2.

* * * * *